United States Patent

West et al.

[11] Patent Number: 6,159,353
[45] Date of Patent: Dec. 12, 2000

[54] CAPILLARY ELECTROPHORETIC SEPARATION SYSTEM

[75] Inventors: Steven J. West, Hull; Carsten Haber, Cohasset, both of Mass.

[73] Assignee: Orion Research, Inc., Beverly, Mass.

[21] Appl. No.: 09/069,483

[22] Filed: Apr. 29, 1998

Related U.S. Application Data

[60] Provisional application No. 60/045,210, Apr. 30, 1997.

[51] Int. Cl.[7] .................................................. B01D 15/08
[52] U.S. Cl. .......................................... 204/601; 204/603
[58] Field of Search ..................................... 204/601, 603

[56] References Cited

U.S. PATENT DOCUMENTS

| | | | |
|---|---|---|---|
| 4,597,298 | 7/1986 | Ruzicka et al. | 73/863.71 |
| 4,816,123 | 3/1989 | Ogan et al. | 204/183.3 |
| 4,908,112 | 3/1990 | Pace | 204/299 |
| 5,126,023 | 6/1992 | Huang et al. | 204/180.1 |
| 5,169,510 | 12/1992 | Lunte et al. | 204/299 |
| 5,194,133 | 3/1993 | Clark et al. | 204/299 |
| 5,223,114 | 6/1993 | Zare et al. | 204/299 |
| 5,244,560 | 9/1993 | Kuhr | 204/299 |
| 5,296,114 | 3/1994 | Manz | 204/180.1 |
| 5,298,139 | 3/1994 | Huang et al. | 204/299 |
| 5,338,427 | 8/1994 | Shartle et al. | 204/299 |
| 5,342,492 | 8/1994 | Dadoo et al. | 204/180.1 |
| 5,358,612 | 10/1994 | Dasgupta et al. | 204/180.1 |
| 5,374,834 | 12/1994 | Geis et al. | 257/239 |
| 5,376,252 | 12/1994 | Ekstrom et al. | 204/299 R |
| 5,403,451 | 4/1995 | Riviello et al. | 204/153.1 |
| 5,429,734 | 7/1995 | Gajar et al. | 204/299 |
| 5,433,838 | 7/1995 | Dasgupta et al. | 204/299 |
| 5,453,170 | 9/1995 | Krstanovic et al. | 204/299 R |
| 5,472,584 | 12/1995 | Rocklin et al. | 204/180.1 |
| 5,479,035 | 12/1995 | Geis et al. | 257/239 |
| 5,480,525 | 1/1996 | Colon | 204/180.1 |
| 5,486,335 | 1/1996 | Wilding et al. | 422/55 |
| 5,494,641 | 2/1996 | Krstanovic | 422/103 |
| 5,545,303 | 8/1996 | Schasfoort | 204/601 |
| 5,573,651 | 11/1996 | Dasgupta et al. | 204/601 |
| 5,580,435 | 12/1996 | Kovacs | 204/603 |
| 5,582,701 | 12/1996 | Geis et al. | 204/451 |
| 5,599,432 | 2/1997 | Manz et al. | 204/451 |
| 5,645,702 | 7/1997 | Witt et al. | 204/501 |
| 5,888,390 | 3/1999 | Craig | 204/601 |
| 5,890,745 | 4/1999 | Kovacs | 205/666 |

FOREIGN PATENT DOCUMENTS

WO 95/10040 4/1995 WIPO .

OTHER PUBLICATIONS

K. Seiler et al., "Planar Glass Chips for Capillary Electrophoresis: Repetitive Sample Injection, Quantitation, and Separation Efficiency", *Anal. Chem.* 1993, 65, 1481–1488.

Nebojsa Avdalovic et al., Determination of Cations and Anions by Capillary Electrophoresis Combined with Suppressed Conductivity Detection, *Anal. Chem.* 1993, 65, 1470–1475.

Purnendu K. Dasgupta et al., "Suppressed Conductometric Capillary Electrophoresis", *Anal. Chem.* 1993, 65, 1003–1011.

D. Jed Harrison, et al., "Capillary Electrophoresis and Sample Injection Systems Integrated on a Planar Glass Chip", *Anal. Chem.* 1992, 64, 1926–1932.

Xiaohua Huang, et al., "End–Column Detection for Capillary Zone Electrophoresis", *Anal. Chem.* 1991, 63, 189–192.

Ross A. Wallingford et al., "Capillary Zone Electrophoresis with Electrochemical Detection", *Anal. Chem.* 1987, 59, 1762–1766.

(List continued on next page.)

*Primary Examiner*—Arun S. Phasge
*Attorney, Agent, or Firm*—Ernest V. Linek; Banner & Witcoff, Ltd.

[57] ABSTRACT

The present invention provides an electrophoretic separation system on a planar chip of glass or plastic material with on-chip FIA (flow injection analysis) injection and one or multiple sets of electrodes for on-column, end-column, off-column electrical or electrochemical, suppressed or unsuppressed, conductiometric, high-frequency contactless conductiometric, potentiometric and amperometric detection.

17 Claims, 20 Drawing Sheets-

OTHER PUBLICATIONS

Xiaohua Huang et al., "On–Column Conductivity Detector for Capillary Zone Electrophoresis", *Anal. Chem.* 1987, 59, 2747–2749.

Thomas J. O'Shea et al., "Capillary Electrophoresis with Electrochemical Detection Employing an On–Column Nafion Joint", *Journal of Chromatography*, 593 (1992) 305–312.

Wim Th. Kok et al., "Sold–State Field Decoupler for Off–Column Detection in Capillary Electrophoresis", *Anal. Chem.* 1993, 65, 2497–2501.

Stephen C. Jacobson et al., "Fused Quartz Substrates for Microchip Electrophoresis", *Anal. Chem.* 1995, 67, 2059–2063.

Petr Kuban et al., "On–Line Dialysis Coupled to a Capillary Electrophoresis System for Determination of Small Anions", *Anal. Chem.* 1997, 69, 1169–1173.

Shen Hu et al., "Amperometric Detection in Capillary Electrophoresis with an Etched Joint", *Anal. Chem.* 1997, 69, 264–267.

Andreas J. Zemann et al., "Contactless Conductivity Detection for Capillary Electrophoresis", *Anal. Chem.* 1998, 70, 563–567.

Jonathan M. Slater et al., "On–Chip Microband Array Electrochemical Detectior for Use in Capillary Electrophoresis", *Analyst*, Nov. 1994, vol. 119, pp. 2303–2307.

Carsten Haber et al., "Potentiometric Detector for Capillary Zone Electrophoresis", *Chimia* 45 (Apr. 1991) Nr. 4.

Jaromir Ruzicka et al., "Integrated Microconduits for Flow Injection Analysis", *Analytica Chimica Acta* 161 (1984) 1–25.

Petr Kuban et al., "New Interface for Coupling Flow–Injection and Capillary Electroph oresis", *Analytica Chimica Acta* 337 (1997) 117–124.

F.M. Everaerts et al., "Isotachophoresis", *Journal of Chromatography Library*—vol. 6. (No date).

A. Manz et al., "Miniaturized Total Chemical Analysis Systems: a Novel Concept for Chemical Sensing", *Sensors and Actuators*,B1 (1990) 244–248.

Carsten Haber et al., "Conductivity Detection in Capillary Electrophoresis—A Powerful Tool in Ion Analysis", *J. Cap. Elec.* 003: 1 1996, pp. 1–11.

James P. Landers, Handbook of Capillary Electrophoresis, Second Edition. (No date).

Richard J. Reay, "Microfabrication Electrochemical Detector for Capillary Electrophoresis", Abstract. (No date).

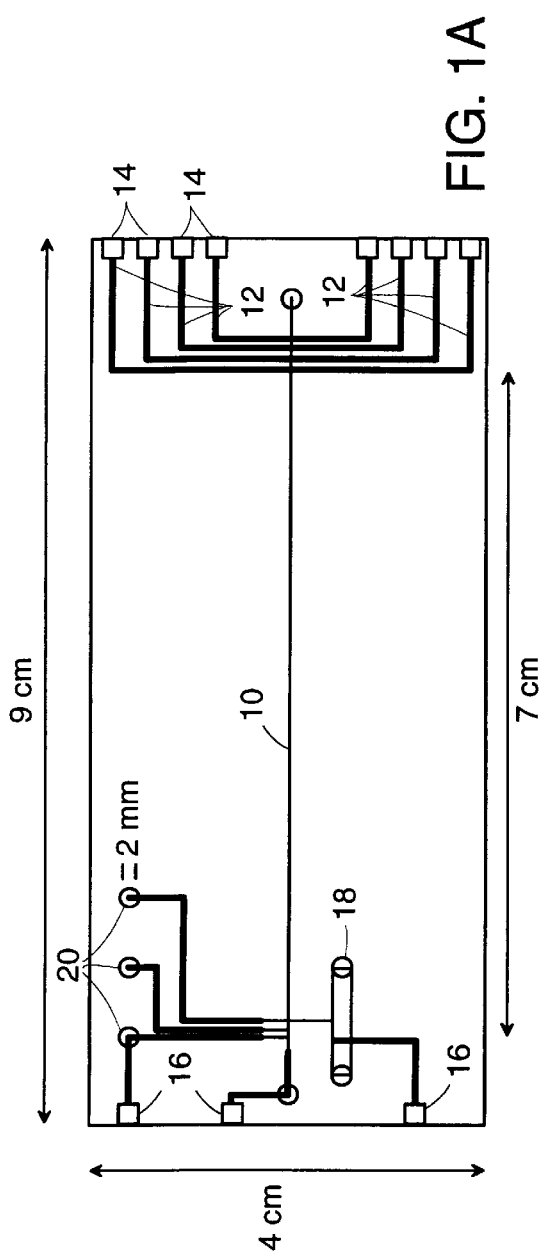
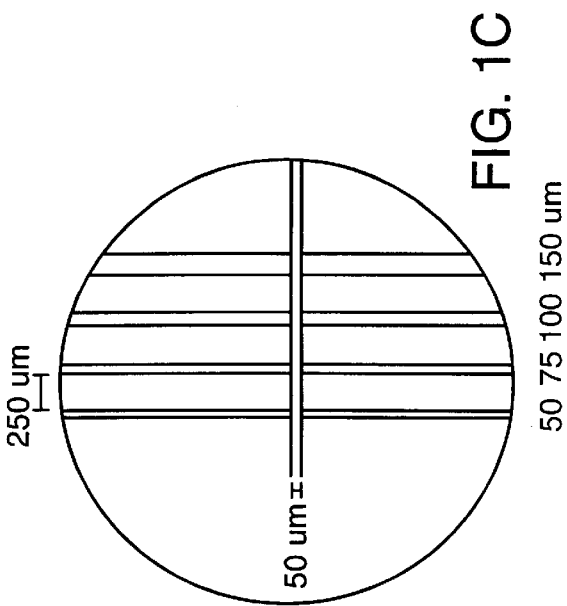
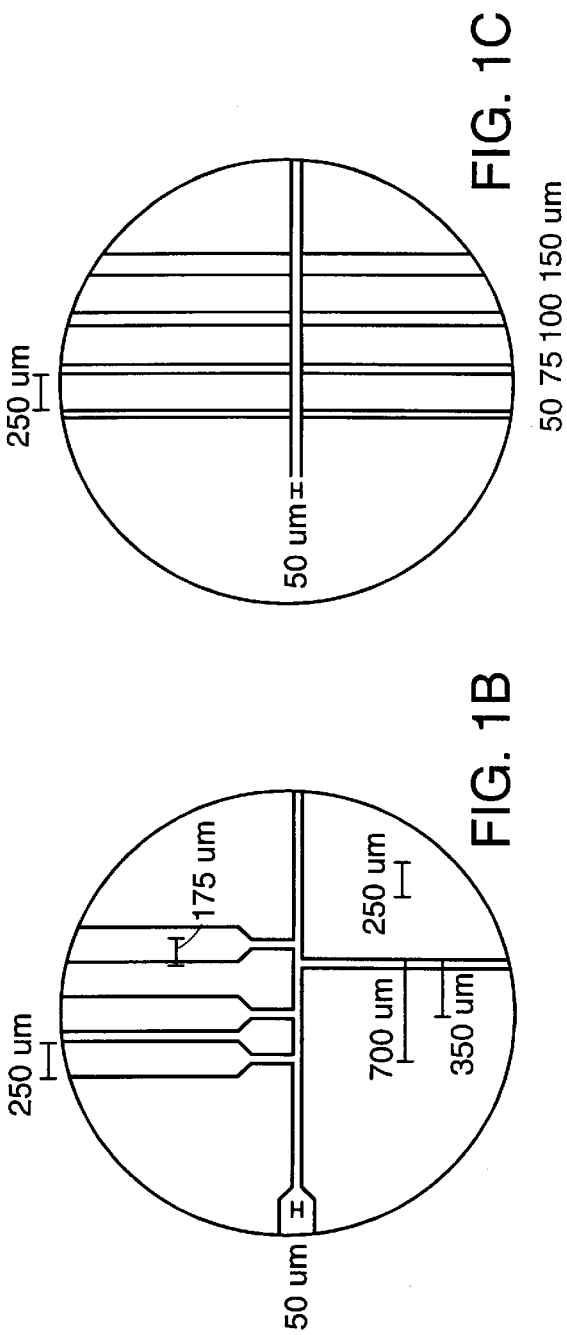

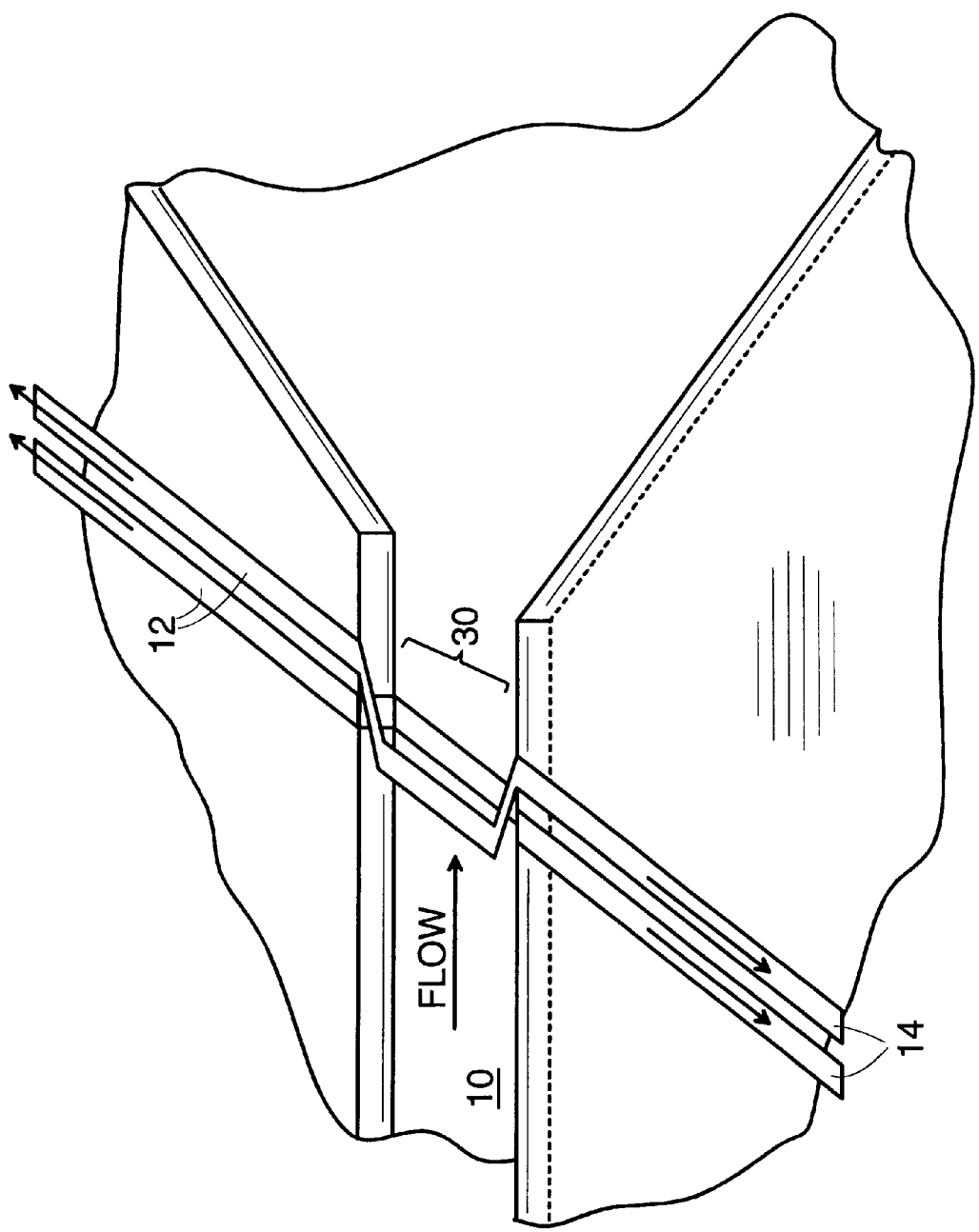

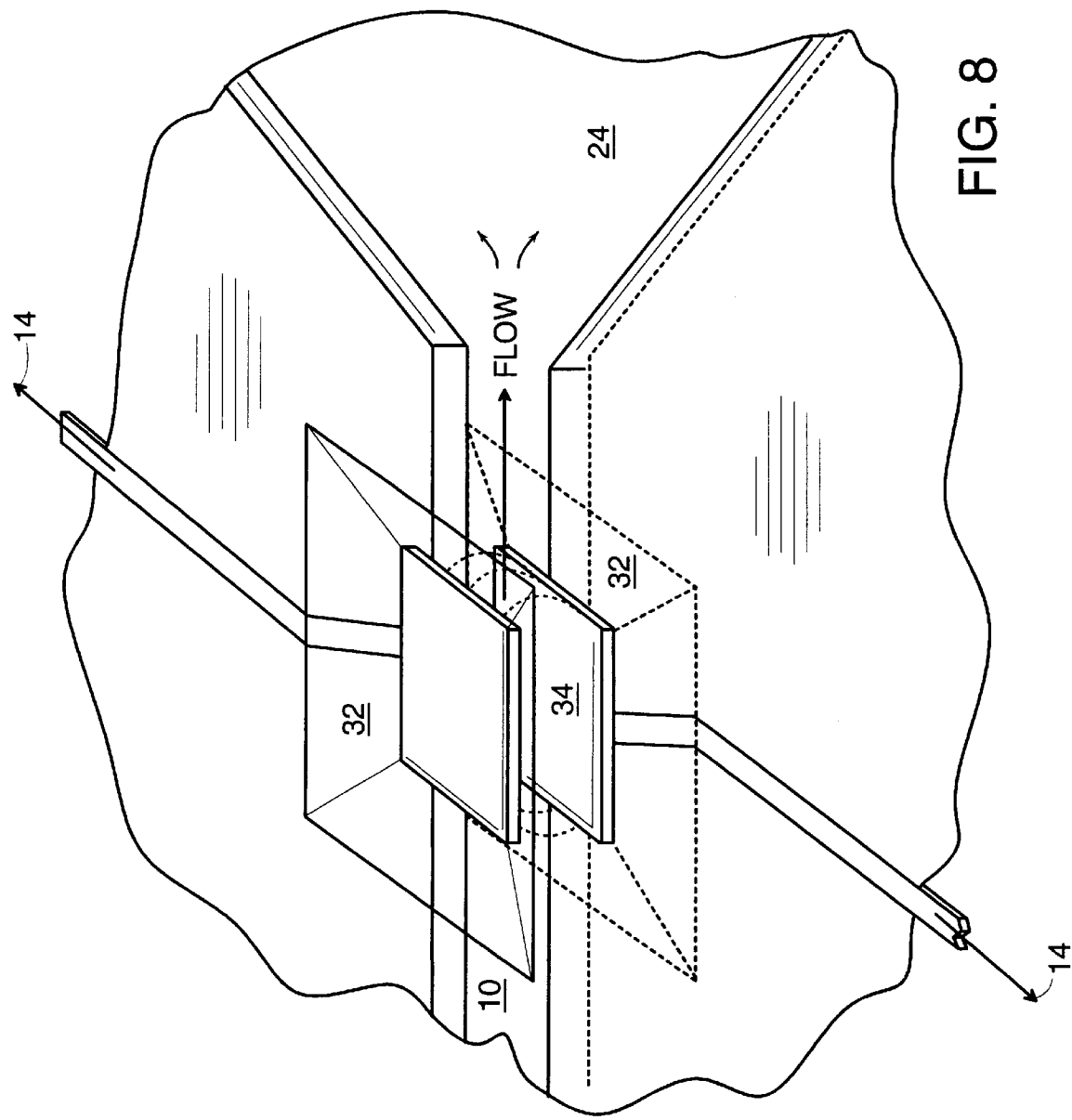

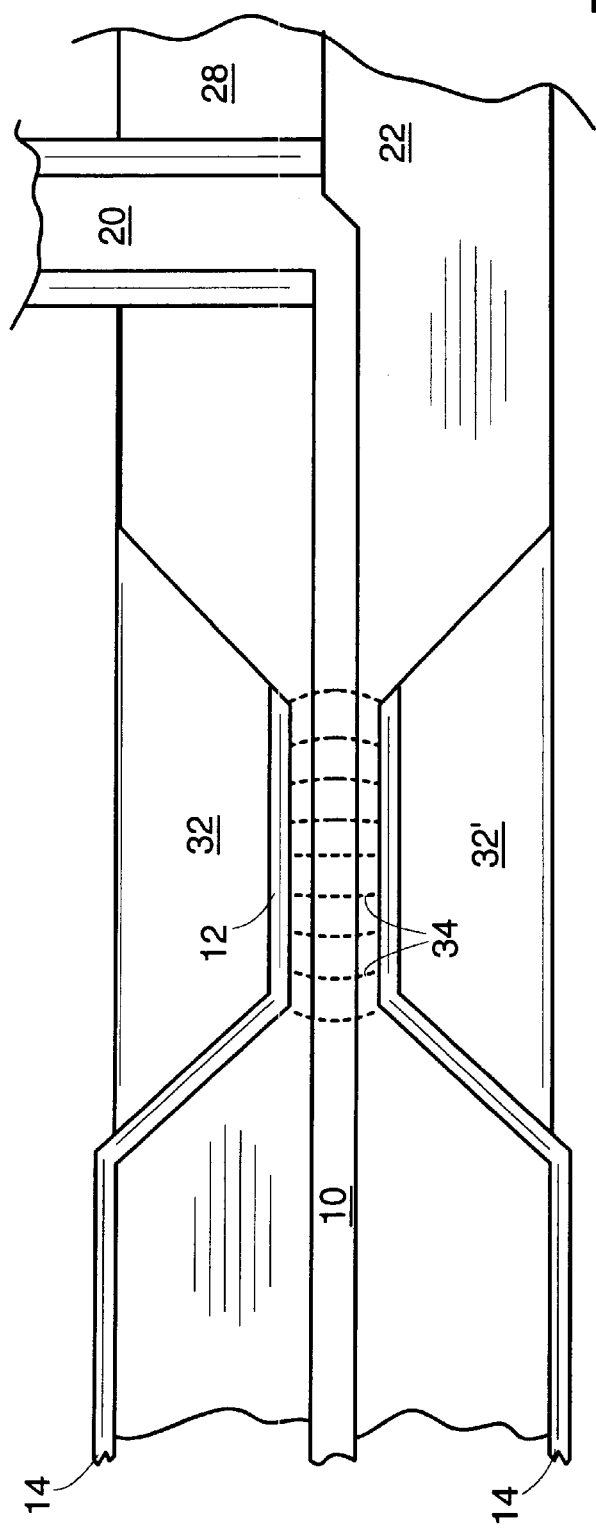

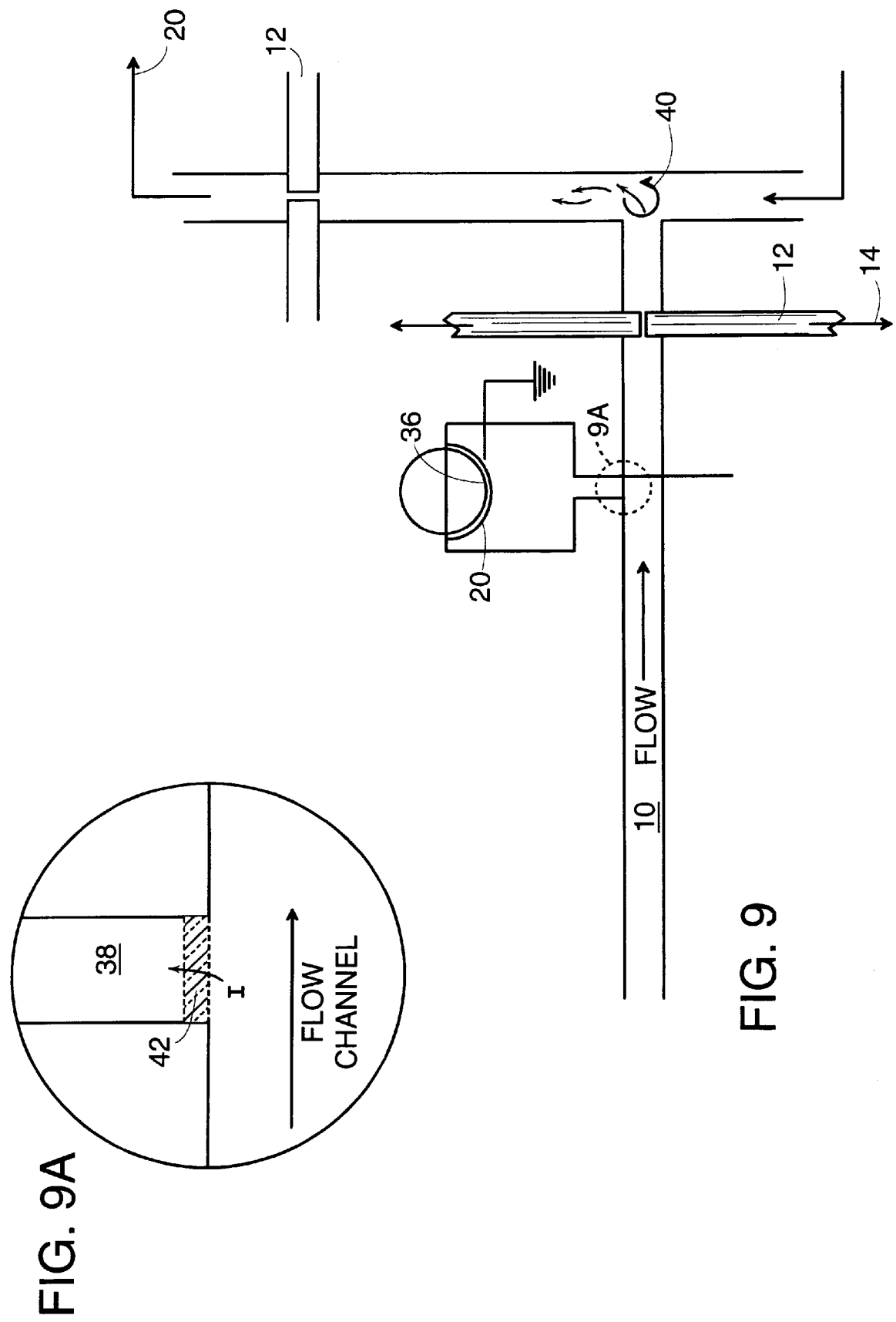

CAPILLARY ELECTROPHORETIC SEPARATION SYSTEM

CROSS REFERENCE TO RELATED APPLICATION

This application claims the benefit of U.S. Provisional Application Serial No. 60/045,210, filed Apr. 30, 1997, the teachings of which are hereby incorporated herein by reference.

BACKGROUND OF THE INVENTION

The present invention is directed to a capillary electrophoretic (CE) separation system. Other such systems are described in the following patents, the disclosures of which are incorporated herein by reference:

U.S. Pat. No. 5,599,432 (Manz), which describes a device and method useful for the electrophoretic separation of fluid substance mixtures;

U.S. Pat. No. 5,582,701 (Geis) which describes an ionic liquid-channel charge coupled device;

U.S. Pat. No. 5,580,435 (Kovacs), which describes a system for detecting components of a sample in electrophoretic separation;

U.S. Pat. No. 5,573,651 (Dasgupta), which describes an apparatus and method for flow injection analysis;

U.S. Pat. No. 5,545,303 (Schasfoort), which describes a system for analyzing the concentration of a number of different ions in a watery solution;

U.S. Pat. No. 5,494,641 (Krstanovic), which describes connectorized capillaries for use with separation instrumentation components;

U.S. Pat. No. 5,486,335 (Wilding), which describes an analysis system based on flow restriction;

U.S. Pat. No. 5,480,525 (Colon), which describes a machine accessible electrochemical detector for capillary electrophoresis;

U.S. Pat. No. 5,479,035 (Geis), which describes an ionic liquid-channel charge coupled device;

U.S. Pat. No. 5,472,584 (Rocklin), which describes a method and apparatus for improved detection of ionic species by capillary electrophoresis;

U.S. Pat. No. 5,453,170 (Krstanovic), which describes an off-column detector for ion separation techniques;

U.S. Pat. No. 5,433,838 (Dasgupta), which describes an electrophoresis system with chemically suppressed detection;

U.S. Pat. No. 5,429,734 (Gajar), which describes a an monolithic capillary electrophoretic device;

U.S. Pat. No. 5,403,451 (Riviello), which describes a method and apparatus for pulsed electrochemical detection using polymer electroactive electrodes;

U.S. Pat. No. 5,374,834 (Geis), which describes an ionic liquid-channel charge-coupled device;

U.S. Pat. No. 5,358,612 (Dasgupta), which describes an electrophoresis system with chemically suppressed detection;

U.S. Pat. No. 5,342,492 (Dadoo), which describes a system for electrokinetic separation and detection where the detection is performed at other than separation electric field;

U.S. Pat. No. 5,338,427 (Shartle), which describes a single use separation cartridge for a capillary electrophoresis instrument;

U.S. Pat. No. 5,298,139 (Huang), which describes an end-column conductivity detector for capillary zone electrophoresis;

U.S. Pat. No. 5,296,114 (Manz), which describes an electrophoretic separating device and electrophoretic separating method;

U.S. Pat. No. 5,244,560 (Kuhr), which describes a method of fabrication for capillary electrophoresis and electrochemical detector for the same;

U.S. Pat. No. 5,223,114 (Zare), which describes an on-column conductivity detector for microcolumn electrokinetic separations;

U.S. Pat. No. 5,169,510 (Lunte), which describes an ion-permeable polymer joint for use in capillary electrophoresis;

U.S. Pat. No. 5,126,023 (Huang), which describes an end-column electrical and electrochemical detector for capillary zone electrophoresis;

U.S. Pat. No. 4,908,112 (Pace), which describes a silicon semiconductor wafer for analyzing micronic biological samples;

U.S. Pat. No. 4,816,123 (Ogan), which describes a method of fabricating capillary electrophoresis separation channels; and U.S. Pat. No. 4,597,298 (Ruzicka), which describes a hydrodynamic sample introducing system.

The following publications provide background information related to the present invention, and to the extent necessary, the disclosures thereof are hereby incorporated herein by reference:

F. M. Everaerts et al., "Isotachophoresis—Theory, Instrumentation and Applications", Elsevier, Amsterdam (1976).

J. Ruzicka, et al., "Integrated microconduits for flow injection analysis", *Anal. Chim. Acta* 161 (1984) 1–25.

X. Huang, et al., "On-column conductivity detector for capillary zone electrophoresis, *Anal. Chem.* 59 (1987) 2747.

R. A. Wallingford, et al., "Capillary zone electrophoresis with electrochemical detection", *Anal. Chem.* 59 (1987) 1762.

A. Manz, et al., "Miniaturized total chemical analysis systems: A novel concept for chemical sensing", *Sens. Act.* B1 (1990) 244–248.

C. Haber, et al., "Potentiometric Detector for Capillary Zone Electrophoresis", *Chimia* 45 (1991) 117–121.

X. Huang, et al. "End-column detection for capillary zone electrophoresis", *Anal. Chem.* 63 (1991) 189.

T. J. O'Shea, et al., "Capillary electrophoresis with electrochemical detection employing an on-column Nafion joint", *J. Chromatogr.* 593 (1992) 305.

D. J. Harrison, et al., "Capillary electrophoresis and sample injection systems integrated on a planar glass chip", *Anal. Chem.* 64 (1992) 1926–1932.

A. Manz, et al., "Miniaturization of separation techniques using planar chip technology", *J. High Res. Chromatogr.* 16 (1993) 433–436.

P. K. Dasgupta, et al., "Suppressed conductometric capillary electrophoresis separation systems", *Anal. Chem.* 65 (1993) 1003.

N. Avdalovic, et al., "Determination of cations and anions by capillary electrophoresis combined with suppressed conductivity detection", *Anal. Chem.* 65 (1993) 1470.

K. Seiler, et al., "Planar glass chips for capillary electrophoresis: Repetitive sample injection, quantitation, and separation efficiency", *Anal. Chem.* 65 (1993) 1481–1488.

W. Kok, et al., "Solid state field decoupler for off-column detection in capillary electrophoresis", *Anal. Chem.* 65 (1993) 2497.

J. R. Reay, et al., "Microfabricated electrochemical detector for capillary electrophoresis", Proc. Solid-State Sensor and Actuator Workshop, Hilton Head (1994), p. 61.

J. M. Slater, et al., "On-chip microband array electrochemical detector for use in capillary electrophoresis", The Analyst 119 (1994) 2303–2307.

S. Jacobson, et al., "Fused quarz substrates for microchip electrophoresis", Anal. Chem. 67 (1995) 2059–2063.

C. Haber, et al., "Conductivity detection in capillary electrophoresis—a powerful tool in ion analysis, J. Cap. Electrophor. 3 (1996) 1–111.

P. Kuban, et al., "New interface for coupling flow-injection and capillary electrophoresis", Anal. Chim. Acta 337 (1997) 117–124.

P. Kuban, et al., "On-line dialysis coupled to a capillary electrophoresis system for determination of small anions", Anal. Chem. 69 (1997) 1169–1173.

C. Haber, "Electrochemical Detection in Capillary Electrophoresis", in: Handbook of Capillary Electrophoresis, 2nd Edition (1997), J. P. Landers (Ed.), CRC Press, Boca Raton, Fla.; pp. 425–447.

S. Hu, et al., "Amperometric detection in capillary electrophoresis with an etched joint", Anal Chem. 69 (1997) 264–267.

A. J. Zemann, et al., "Contactless conductivity detection for capillary electrophoresis", Anal. Chem. 70 (1998), 563–567.

SUMMARY OF INVENTION

The present invention provides a capillary electrophoretic separation system formed on a planar chip, preferably made of glass or plastic material. The preferred chip comprises at least two wafers, one or more of which is provided with one or more separation channels and one or more detection electrodes, designed for either on-column, end-column, off-column electrical or electrochemical detection techniques. These detection techniques include, for example, suppressed or unsuppressed, high-frequency contactless conductiometric, potentiometric and amperometric analyses.

In summary, there are four preferred embodiments described herein for the implementation of an on-chip electrical/electrochemical detection system for electrophoretic ion (cation and/or anion) analysis:

The first preferred embodiment is an "on-column electrode arrangement." In this embodiment, the electrodes are patterned directly into the separation channel. The patterns of the electrodes can be varied, for example, top wafer, bottom wafer or both (a floor and/or ceiling design), and each such design can use one or multiple electrodes per channel. The electrodes are directly exposed to the driving current in this embodiment. In this embodiment, the driving current may create charge-transfer reactions on the electrode surface. This could result in gas formation on the electrode, that in turn would lead to baseline drift and noise interferences. However, such interferences can be reduced or eliminated by appropriate electrode geometry, precise position alignment, material, electrolyte composition, additives, electrode passivation and optimizing/adjusting electrophoretic separation parameter.

The second preferred embodiment is an "end-column electrode arrangement." In this embodiment, the electrodes are patterned at a short distance behind the separation channel into a larger electrically grounded reservoir. The possible electrode geometrys and arrangements are similar or identical to those of the previous embodiment (e.g., top wafer, bottom wafer or both, e.g. floor/ceiling design, one or multiple electrodes per channel etc.). The electrophoretic driving current/current density in the larger reservoir is sharply reduced, which potentially eliminates the probability of detrimental charge-transfer reactions and therefore facilitates detection sensitivity.

A potential disadvantage of this embodiment is a finite amount of zone broadening which increases proportionally to the distance of the electrodes behind the column outlet.

The third preferred embodiment of this invention is an "off-column electrode arrangement." In this embodiment, the detection electrodes are patterned downstream of a conductive joint, which shunts off the electrophoretic current prior to the point of detection. The electrodes are therefore at zero (ground) potential and experience little or no interferences arising from current-related charge-transfer reactions.

A slight drawback to this embodiment arises from the changing flow profile, which introduces finite zone broadening due to the hydrodynamic flow profile in the current-free detection segment of the separation channel.

The fourth preferred embodiment of this invention is a "contactless electrode arrangement." In this embodiment, the electrodes are patterned into a recess on top and on the bottom of the separation wafer with a thin layer of glass separating the active metal from the fluid in the channel. Contactless conductiometric detection is enabled by use of a high-frequency AC waveform. Detrimental charge-transfer reactions are eliminated due to galvanic separation between electrodes and electrolyte/electrophoretic current.

The details of this invention will be found in the drawings accompanying this specification and the detailed description of each, as provided below.

BRIEF DESCRIPTION OF THE DRAWINGS

FIG. 1A illustrates one preferred embodiment of a chip composed of two planar wafers bonded or sealed together, thus forming an enclosed manifold of trenches, several centimeters in length and width; showing in FIG. 1B one form of patterned trenches for the injection side of said chip, and at FIG. 1C an array of detection electrodes in direct contact and on-column position with the separation channel of said chip.

FIG. 2A shows the top and bottom wafers separated, and FIG. 2B shows them joined together.

FIGS. 6 and 6A illustrate a 'floor-ceiling'-type on-column position arrangement of the metal band electrodes.

FIGS. 8 and 8A show two metal electrodes (as large electrode pads) patterned into a trapezoidal recess made in both the top and the bottom wafers.

FIG. 9 illustrates an on-chip arrangement of suppressed off-column conductivity detection.

FIG. 9A illustrates a micromachined conductive (porous) joint, which is produced by etching a side channel towards the separation channel.

DETAILED DESCRIPTION OF THE INVENTION

As illustrated in the Figures accompanying this specification, the present invention provides an electrophoretic separation system on a planar chip of glass or plastic material with on-chip FIA (flow injection analysis) injection and one or multiple set of electrodes for on-column, end-column, off-column electrical/electrochemical (suppressed /unsuppressed conductiometric, high-frequency contactless conductiometric, potentiometric and amperometric) detection.

FIG. 1A illustrates one preferred embodiment of a chip composed of two planar wafers bonded or sealed together, thus forming an enclosed manifold of trenches, several centimeters in length and width. Typically the FIG. 1A chip is about 9 cm long and about 4 cm wide, providing a separation channel about 7 cm in length. Liquid inlet and outlet ports (left side) are each about 2 mm in diameter and a preferred location of the FIA bypass is shown. The detection electrodes are shown on the right side of the chip. A plurality of contact pads are provided at each end of the chip allow the electrophoretic current to pass through the chip.

FIG. 1B illustrates one preferred form of patterned trenches for the injection side of said chip. The main separation channel is about 50 um in diameter and the liquid inlet and outlet ports can vary as illustrated from 250 um, 175 um, etc.

FIG. 1C illustrates a preferred array design for the detection electrodes, each spaced about 250 nm from each other, and varying in width as shown —50 um, 75 um, 100 um and 150 um. Each electrode shown is in direct contact and on-column position with the separation channel of said chip.

Figure 2:
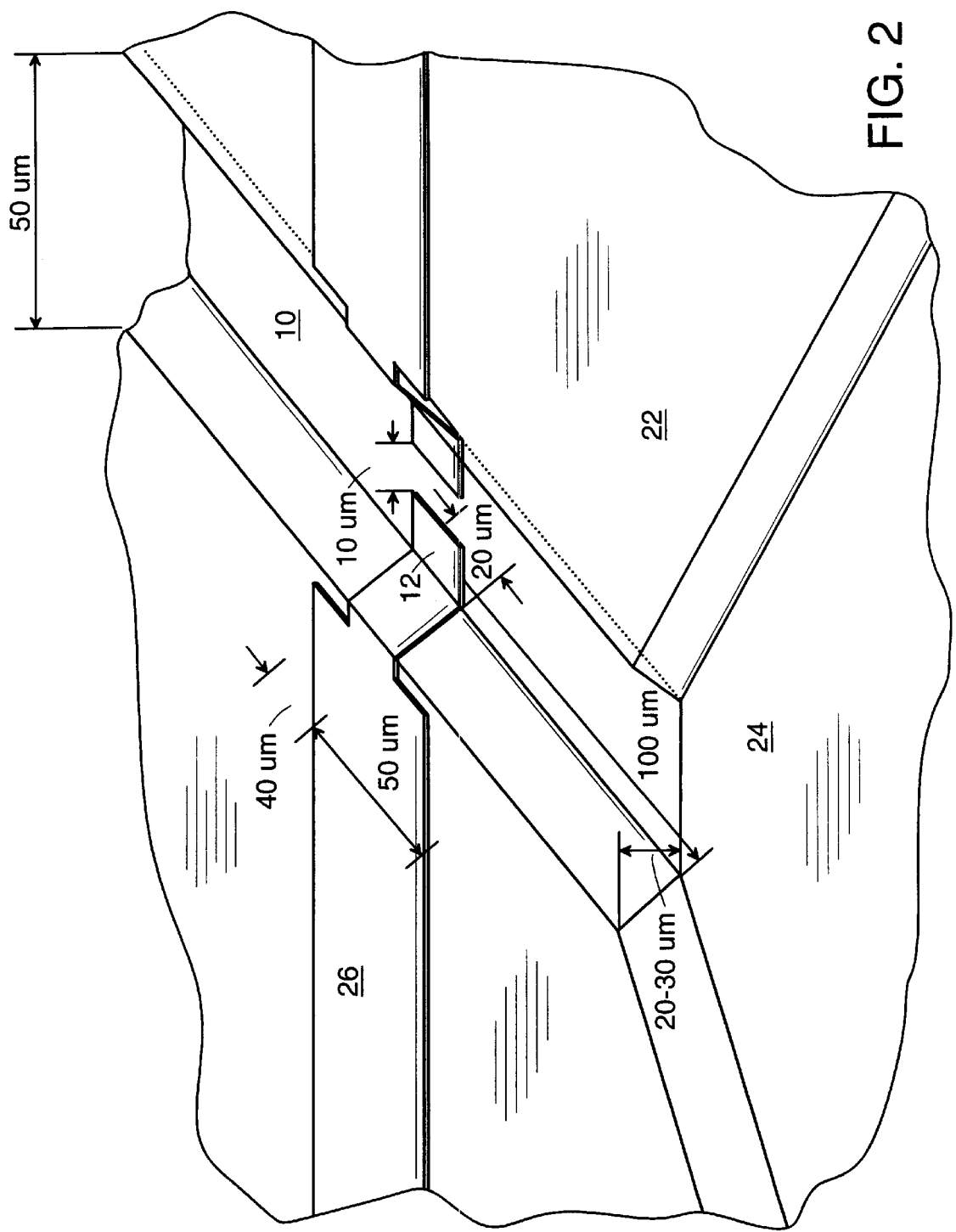
FIG. 2 illustrates a preferred detection electrode arrangement showing a pair of metal band electrodes in direct contact with the liquid in the separation channel.

FIG. 2 illustrates a preferred detection electrode arrangement showing a pair of metal band electrodes in direct contact with the liquid in the separation channel. The two electrodes are patterned as a diametrically opposed pair on the trapezoidal channel walls (on-column position) down into the channel in the bottom wafer.

In the illustrated embodiment, the channel depth is about 20–30 um, and the width of each electrode outside the channel is about 50 um, whereas inside the channel the electrode width decreases to about 20 um. The gap between the two electrodes is about 10 um, and the distance from the edge of the electrodes to the detection reservoir is about 100 um. The channel width at the top of the trapezoid is about 50 um, and at the bottom is about 30 um. Advantageously, each electrode surface is provided with rounded corners.

Figure 2A:
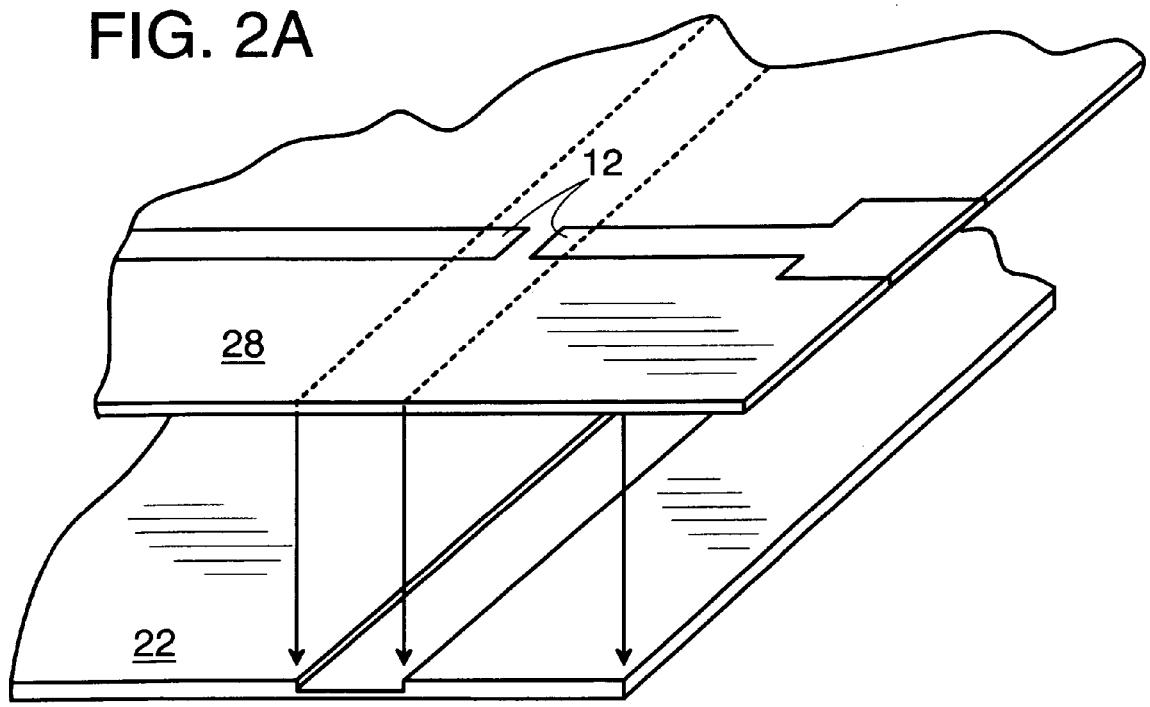
FIGS. 2A and 2B illustrate a similar detection electrode arrangement with a pair of metal band electrodes patterned onto the top wafer.
Figure 2B:
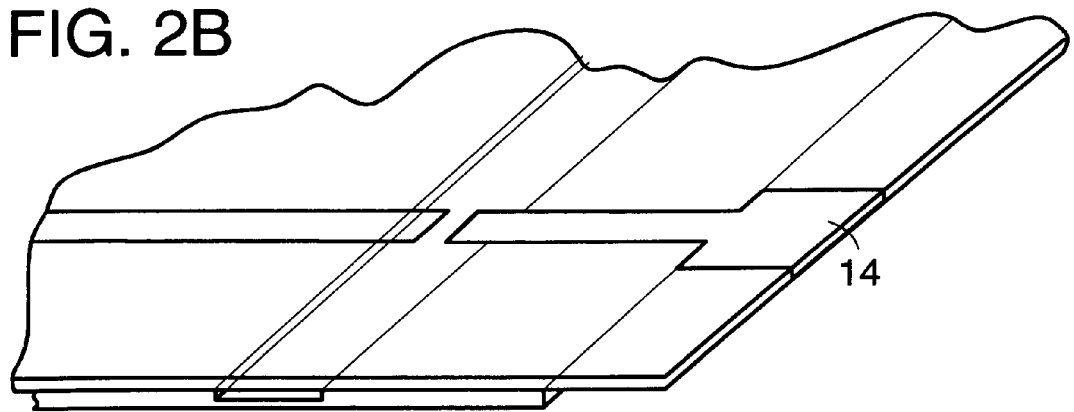

FIGS. 2A and 2B illustrate a similar detection electrode arrangement with a pair of metal band electrodes patterned onto the top wafer. The electrodes are contacted appropriately with the separation channel by precisely bond-aligning the two wafer components (on-column position).

The lower wafer typically holds the channel structure which may be formed by known micromachining techniques, e.g., photolithographical and wet-chemical etching procedures, laser ablation, electroforming-, microcontact printing-, microstamping-, micromolding-, microcasting-, embossing techniques, to name a few. The metal band electrodes are connected to accessible contact pads located at the edges of the chip (see, FIGS. 2A and 2B); the upper wafer contains holes that serve to fill the annealed wafer structure with liquids (sample, electrolyte, etc.). The whole design may be compacted in size and geometry (e.g., by serpentining the separation channel) in order to permit the arrangement of multiple similar microstructures on one single chip. The top and bottom wafer are thermally bonded, clamped or sealed together to form an annealed chip structure.

Figure 3:
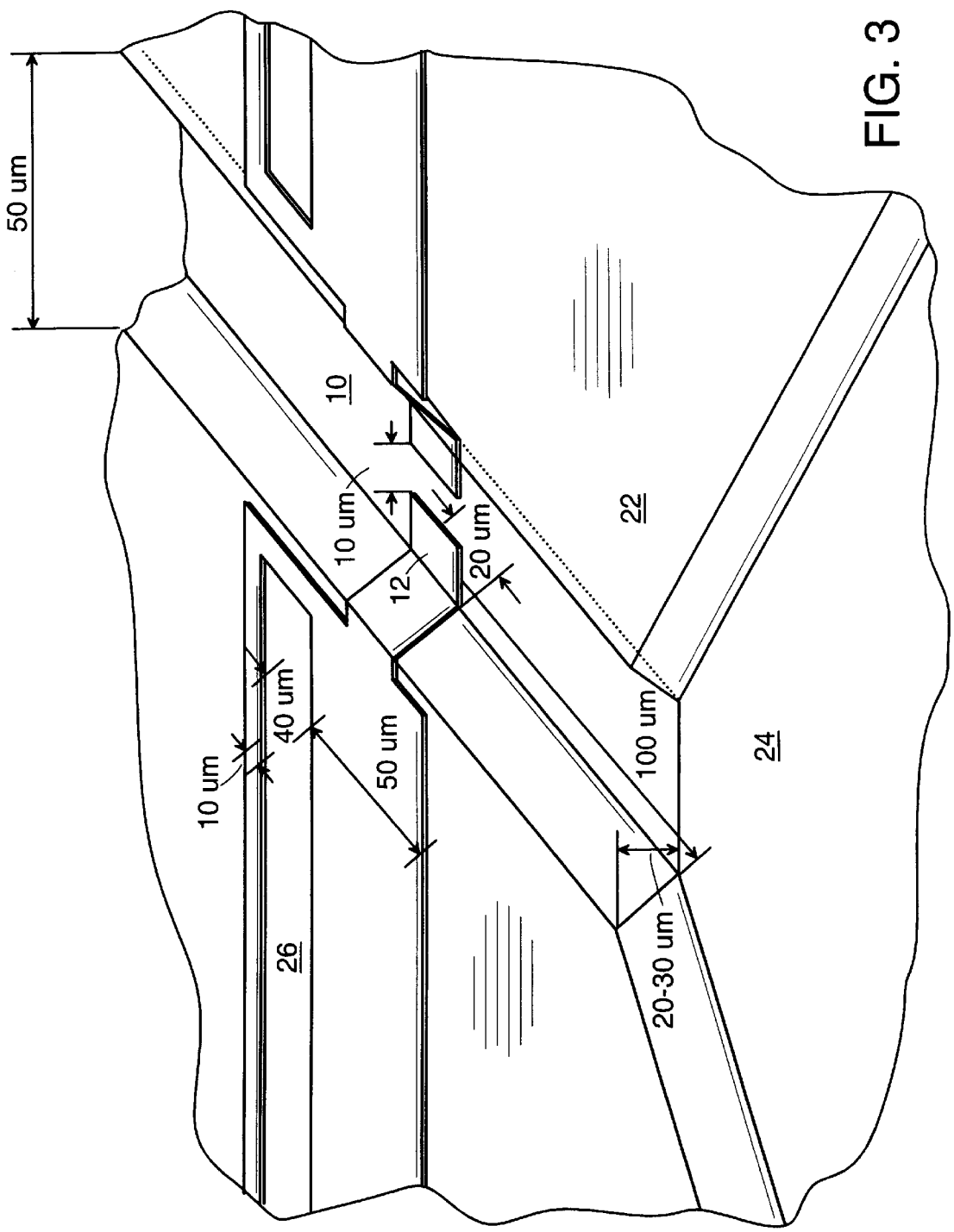
FIG. 3 is an extension of FIG. 2, whereby two additional contact leads are attached on the onset of the band-electrode surface.

FIG. 3 is an extension of FIG. 2, whereby two additional contact leads are attached on the onset of the band-electrode surface. The double-lead arrangement is advantageous for better signal measurement and transduction.

In this illustrated embodiment, the channel depth is about 20–30 um, and the width of each electrode outside the channel is about 50 um, whereas inside the channel the electrode width decreases to about 20 um. The gap between the two electrodes is about 10 um, and the distance from the edge of the electrodes to the detection reservoir is about 100 um. The channel width at the top of the trapezoid is about 50 um, and at the bottom is about 30 um. Again, each electrode surface is provided with rounded corners. In this embodiment, each electrode is provided with an additional contact lead about 10 um in width, separated from the main body by about 40 um.

Figure 4:
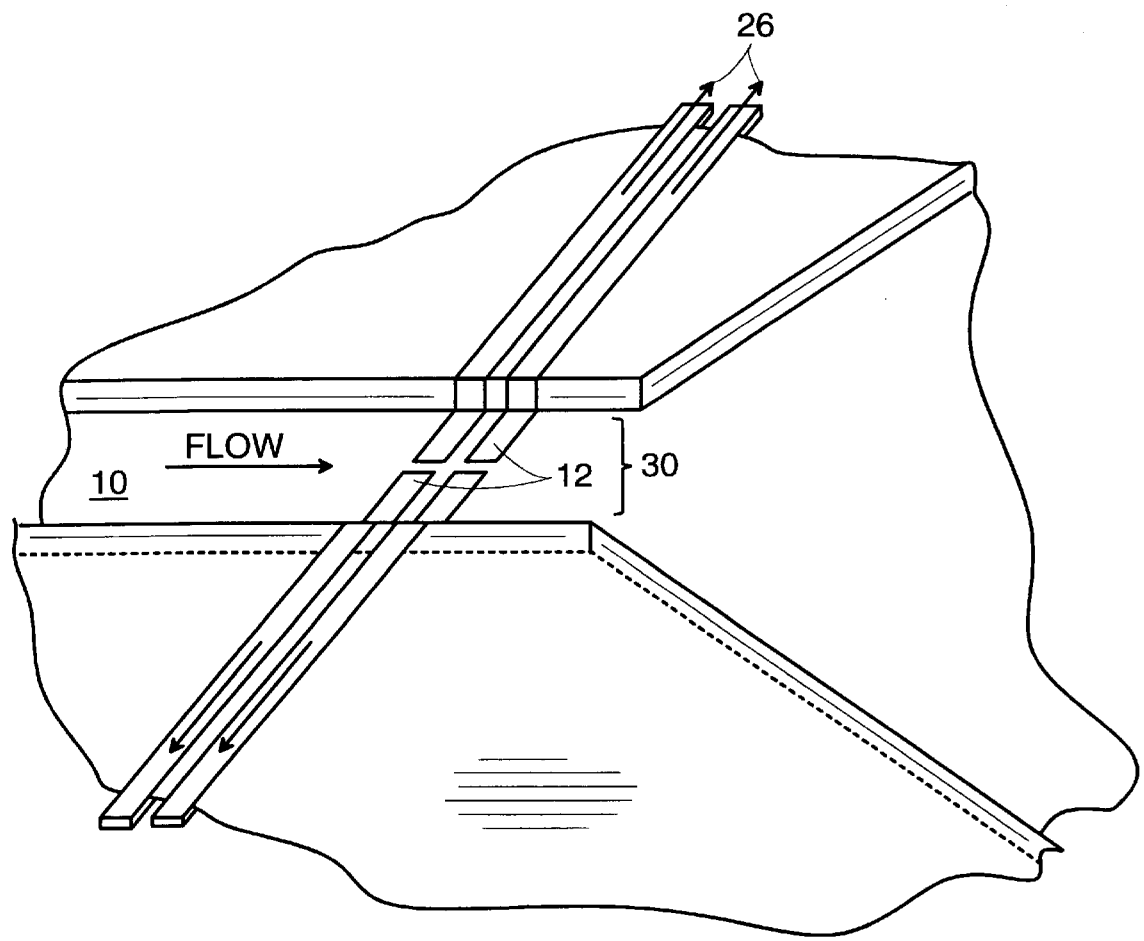
FIGS. 4 and 4A show a four-electrode conductivity detection arrangement with two pairs of metal band electrodes in direct contact with liquid in the separation channel.
Figure 4A:
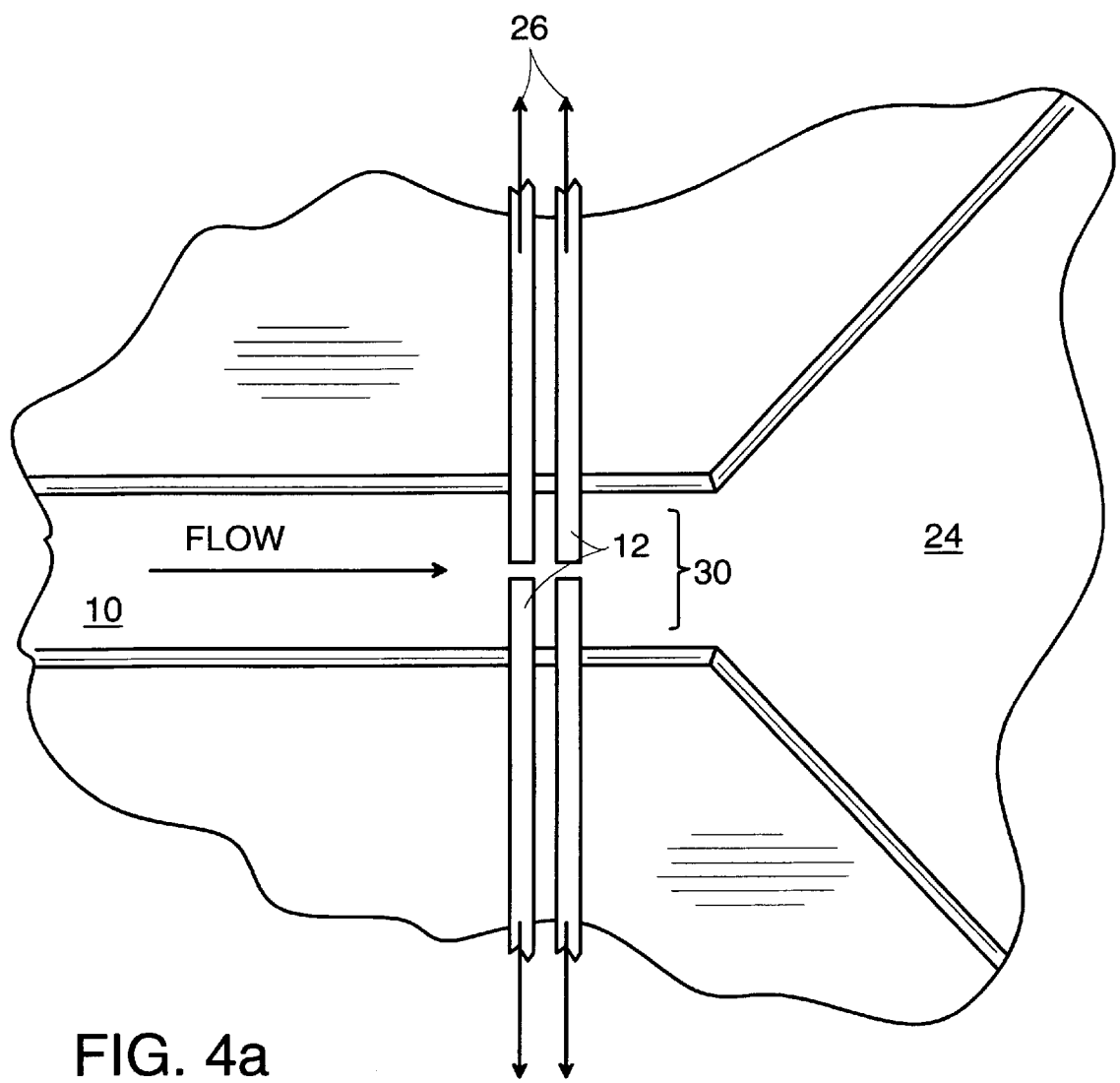

FIGS. 4 and 4A show a preferred four-electrode conductivity detection arrangement with two pairs of metal band electrodes in direct contact with liquid in the separation channel. The electrodes are patterned diametrically opposed on the trapezoidal channel walls (on-column position). The four-electrode measurement technique minimizes effects from electrode polarization and contamination, as well as error from cable- and connector resistance. Drive (current) electrodes and sense (voltage) electrodes may differ in size and position arrangement along the channel.

In FIGS. 4 and 4A, the flow direction in the separation channel is from left to right, across the electrode gap and into the detection region, to large reservoir on the right side.

Figure 5:
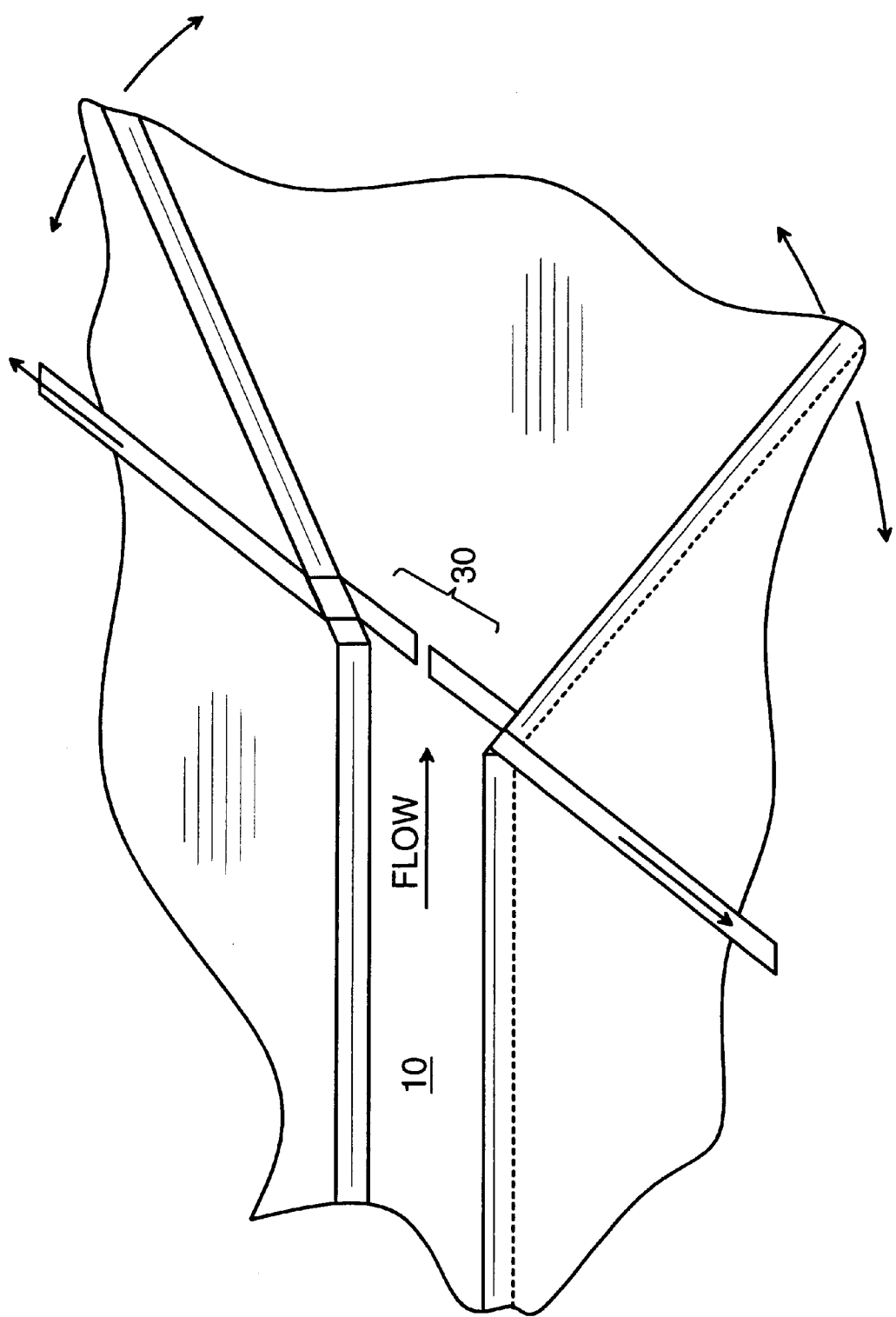
FIGS. 5 and 5A show two diametrically opposed electrodes that are patterned at a short distance behind the separation channel into a larger reservoir.
Figure 5A:
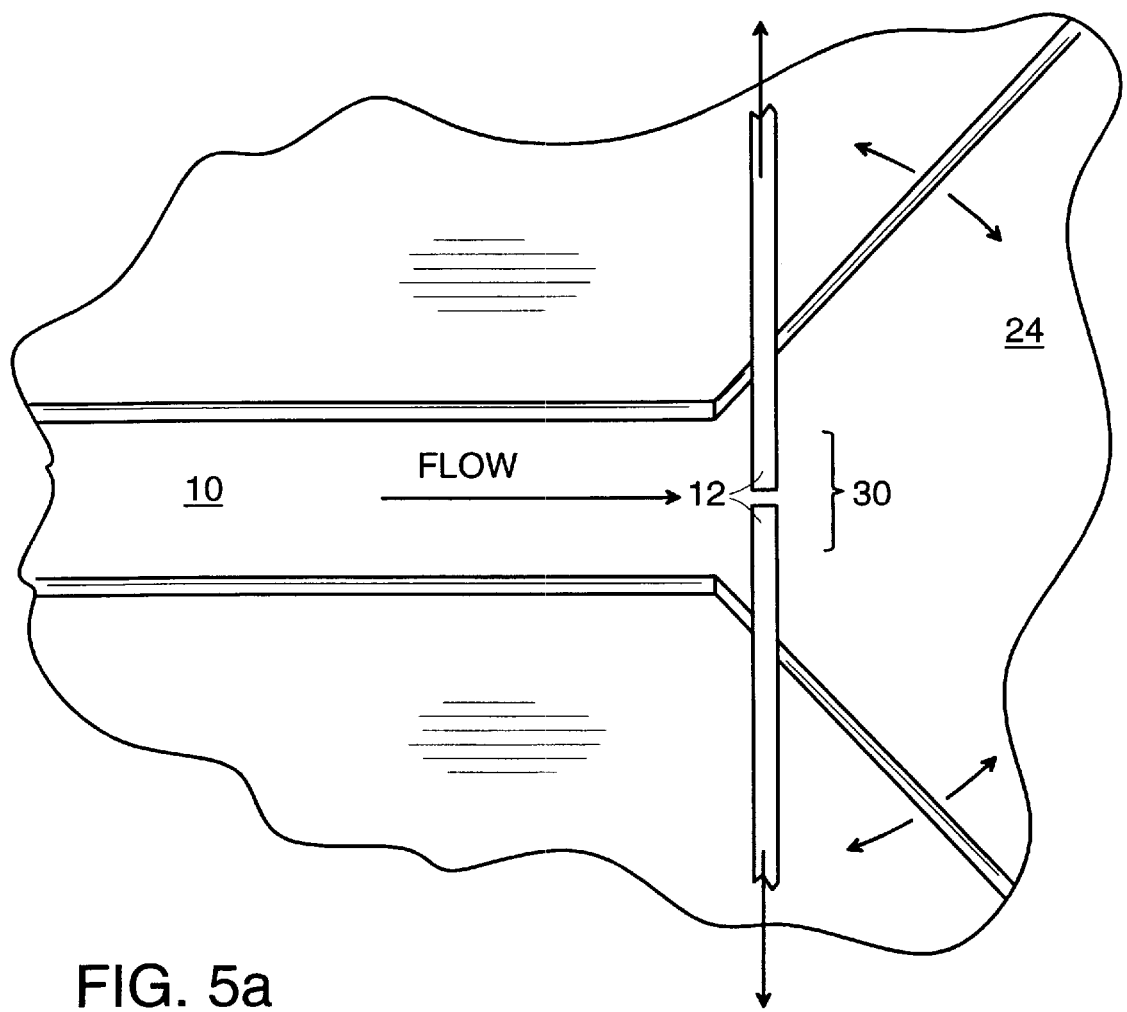

FIGS. 5 and 5A show another preferred embodiment, wherein two diametrically opposed electrodes are patterned at a short distance behind the end of the separation channel and at the entrance to the large reservoir (end-column position). The flow direction through the separation channel is from left to right, across the electrode gap and into the detection region, now located in the reservoir on the right side.

Figure 6A:
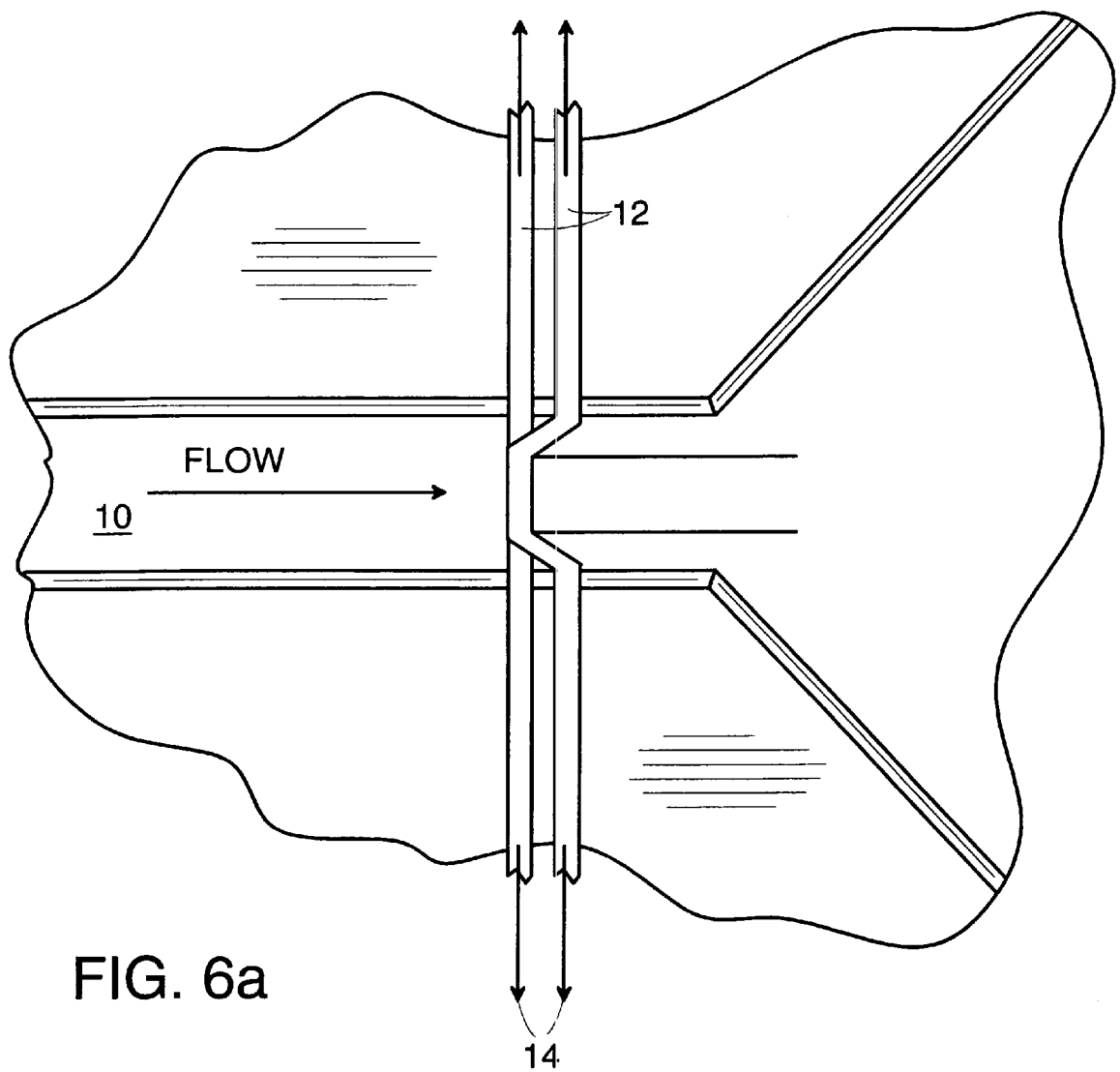

FIGS. 6 and 6A illustrate a preferred 'floor-ceiling'-type on-column position arrangement of the metal band electrodes, whereby one electrode is patterned on the bottom wafer and cuts perpendicular through the separation channel. The other electrode is patterned in a U-shaped geometry slightly offset on the top wafer. Both wafer components are precision aligned and bonded together, thereby forming an annealed structure of two isolated electrodes at the top and bottom of the channel (floor-ceiling and on column position). The flow direction in the separation channel is from left to right, across the electrode gap and into the detection region, and then into the large reservoir on the right side.

Figure 7:
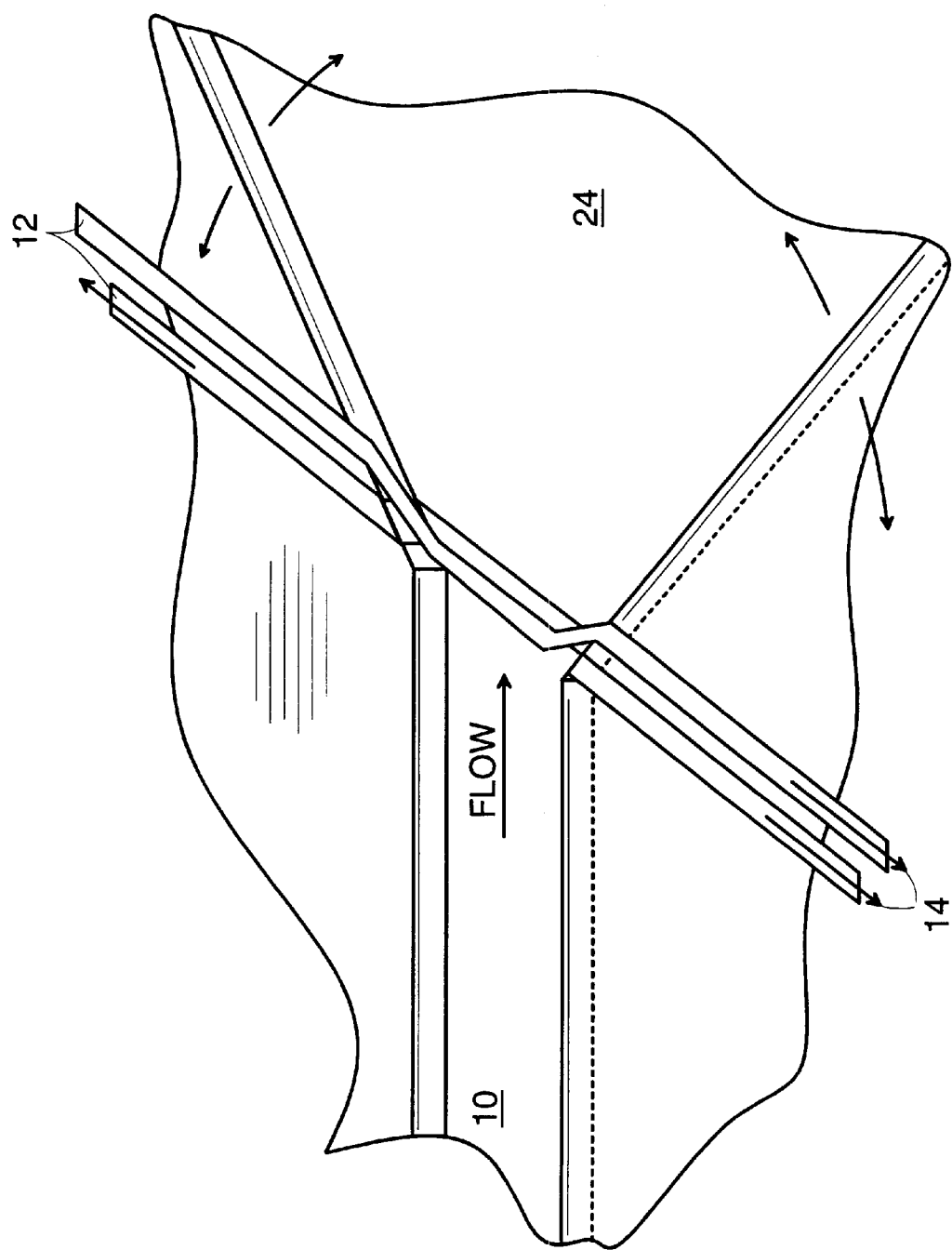
FIGS. 7 and 7A illustrate a similar 'floor-ceiling'-type arrangement, whereby the top and bottom electrode are patterned at a short distance behind the separation channel into a larger reservoir.
Figure 7A:
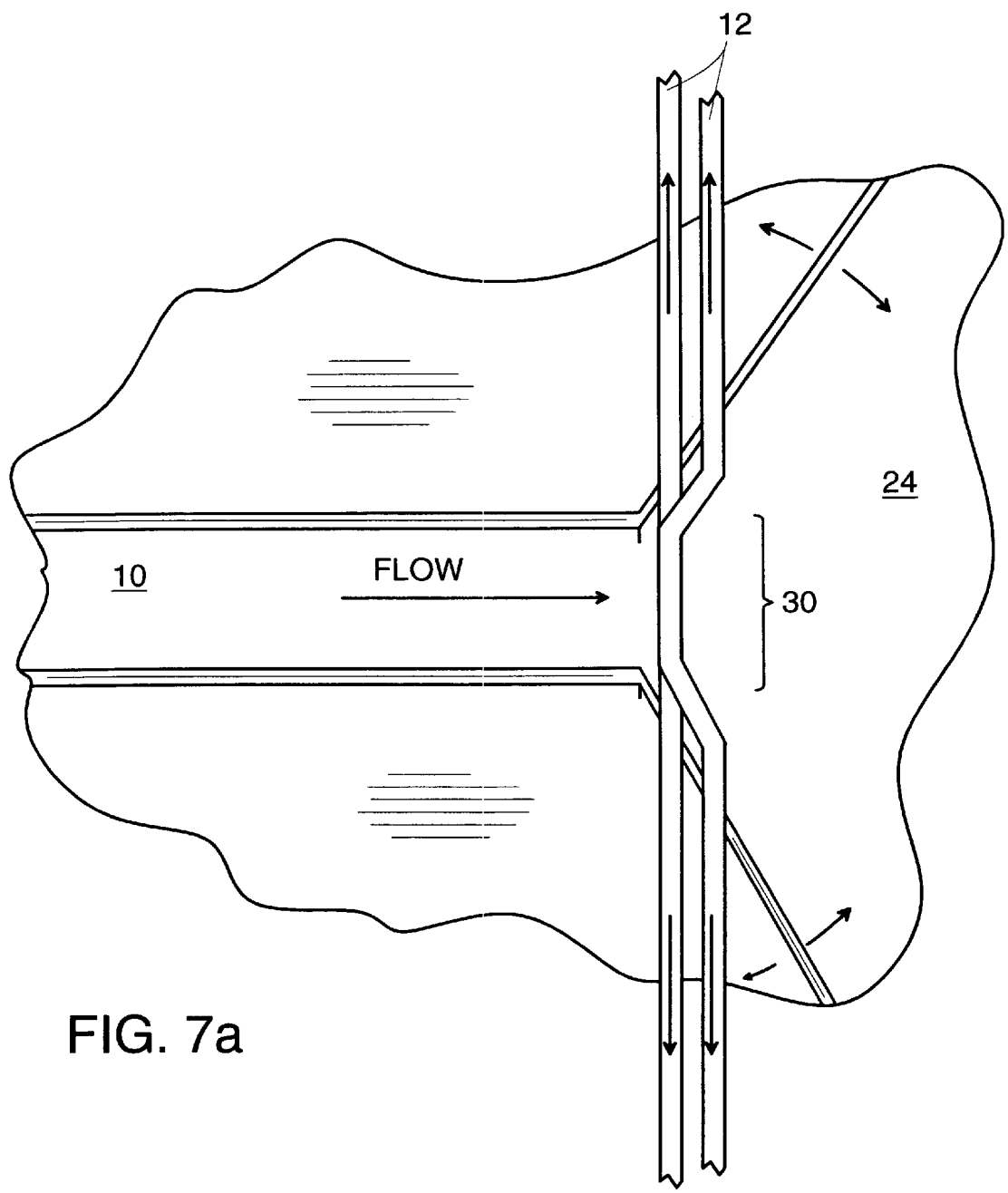

FIGS. 7 and 7A illustrate another 'floor-ceiling'-type arrangement, whereby the top and bottom electrodes are patterned at a short distance behind the separation channel into a larger reservoir (end-column position). The flow direction in the separation channel is from left to right, across the electrode gap and into the detection region, located in the large reservoir on the right side.

FIGS. 8 and 8A show another preferred embodiment, wherein the two metal electrodes are each patterned into a trapezoidal recess formed in both the top and the bottom wafers. The electrodes are advantageously shaped as square or rectangular "pads" and the two pads are precision-aligned above and below the separation channel and remain electrically isolated by a residual thin layer of glass. Therefore they are not in physical contact with the liquid flowing through the separation channel. Both electrodes are operated with a high-frequency alternating current (AC) source, which enables contactless conductivity detection measurement of the fluid passing through the separation channel. The flow direction in the separation channel is from left to right, across the electrode gap and into the detection region, located in the entrance of the large reservoir on the right side.

FIG. 9 illustrates a preferred on-chip arrangement for suppressed off-column conductivity detection. The electrophoretic current is grounded by means of a porous membrane (e.g., porous glass, frit material, conductive or permeable polymer membrane) prior to the first set of detection electrodes. The bulk liquid of the separation channel is pushed by the momentum of the electroosmotic flow past the first set of electrodes into a mixing-'T' where it reacts with suppressor liquid. This arrangement utilizes a second set of detection electrodes behind the point of mixing capable of detecting the passing analyte zones in a low-conductivity (=suppressed) background.

As illustrated, two sets of electrodes are provided, the first set, located in the separation channel provide off-column detection and the second set, past the mixing point, provide suppressed conductivity detection. Flow passes from left to right, past the grounded reservoir filled with electrolyte, which is also provided with a liquid inlet/outlet port. A suppressor liquid is introduced below the mixing point, and waste liquid exits after the second electrode set.

FIG. 9A [shown as an exploded drawing on FIG.9] illustrates a micromachined conductive (porous) joint, which is produced by etching a side channel toward the separation channel. When the glass wall between both channels is thin enough, it becomes a porous glass membrane permitting small buffer ions to penetrate and thus enable electrical transport between the compartments.

The side channel is connected to a larger reservoir having one or more holes for fluid-inlet and outlet and a metal electrode to electrically ground the compartment. The fluid compartment is located upstream to an electrical/ electrochemical detector and siphons the electrophoretic current from the separation channel. The fluid is transported to the electrical and/or electrochemical detector by the momentum of the electroosmotic flow through the first electrodes—off-column detection.

The conductive membrane can also be produced using frit-material or by casting a conductive or permeable polymer membrane (e.g., Nafion) into the side channel.

Figure 10:
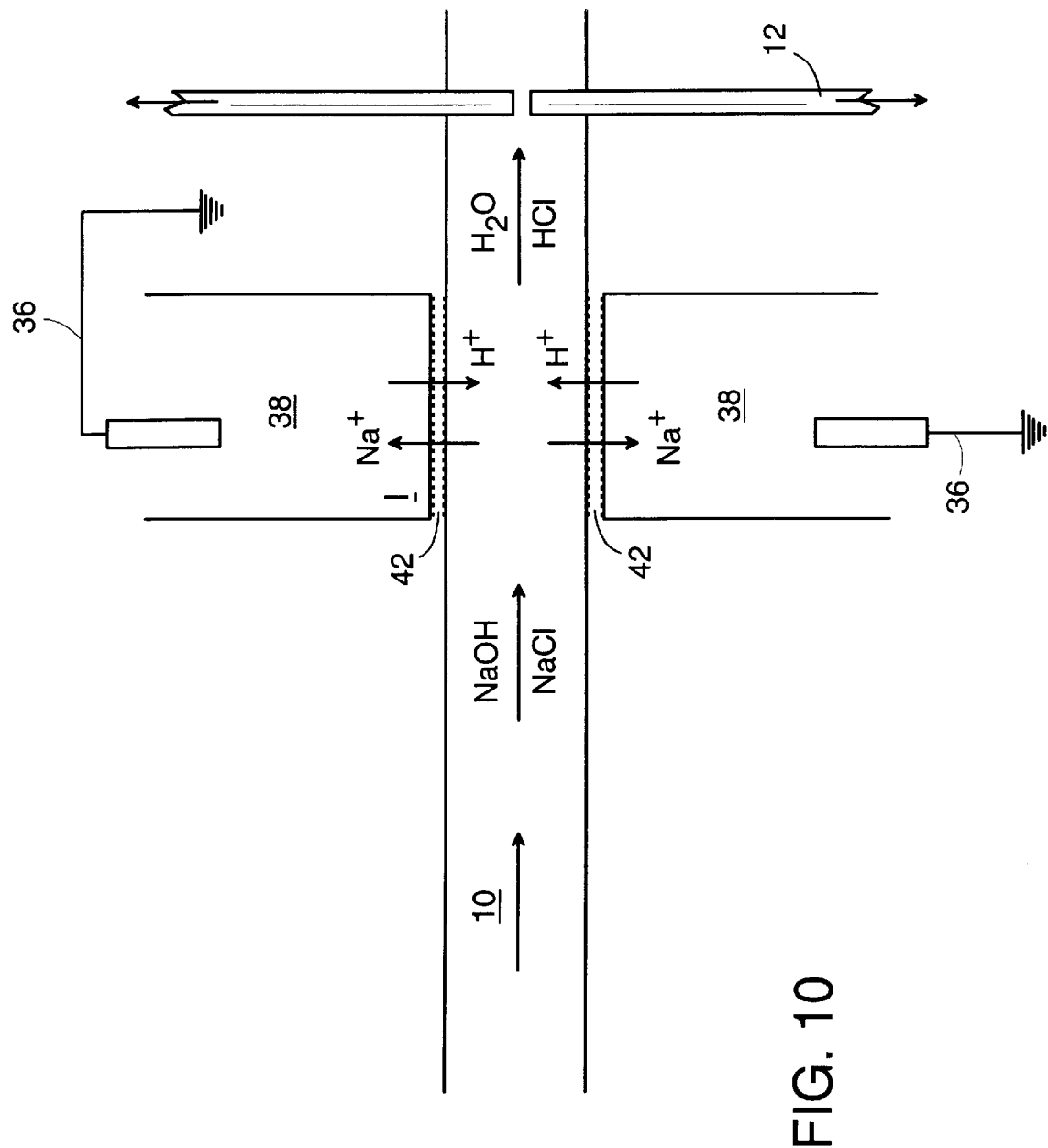
FIG. 10 illustrates an on-chip membrane-suppressed/off-column conductivity detection scheme.

FIG. 10 illustrates another preferred on-chip membrane-suppressed/off-column conductivity detection scheme. The separation channel is contacted prior to the point of detection with a side compartment separated by a porous membrane as described previously (see, FIG. 9A). The liquid in the compartment is composed to chemically complement the background electrolyte in a way that the background conductivity is considerably lowered by ion-exchange upon contact (chemical suppression).

In the illustrated embodiment, NaOH and NaCl flow through the separation channel up to the ion exchange compartments where Na+ ions flow into the side channels and H+ ions flow from the side channels into the separation channel, providing $H_2O$ and HCl which pass by the detection electrodes. The analyte response thus increases, while detection noise and interferences are sharply reduced via siphoning off the electrophoretic current (I) and transferring the background electrolyte into a less conductive compound. The overall detection limits are thus decreased 25–100 times.

Figure 11:
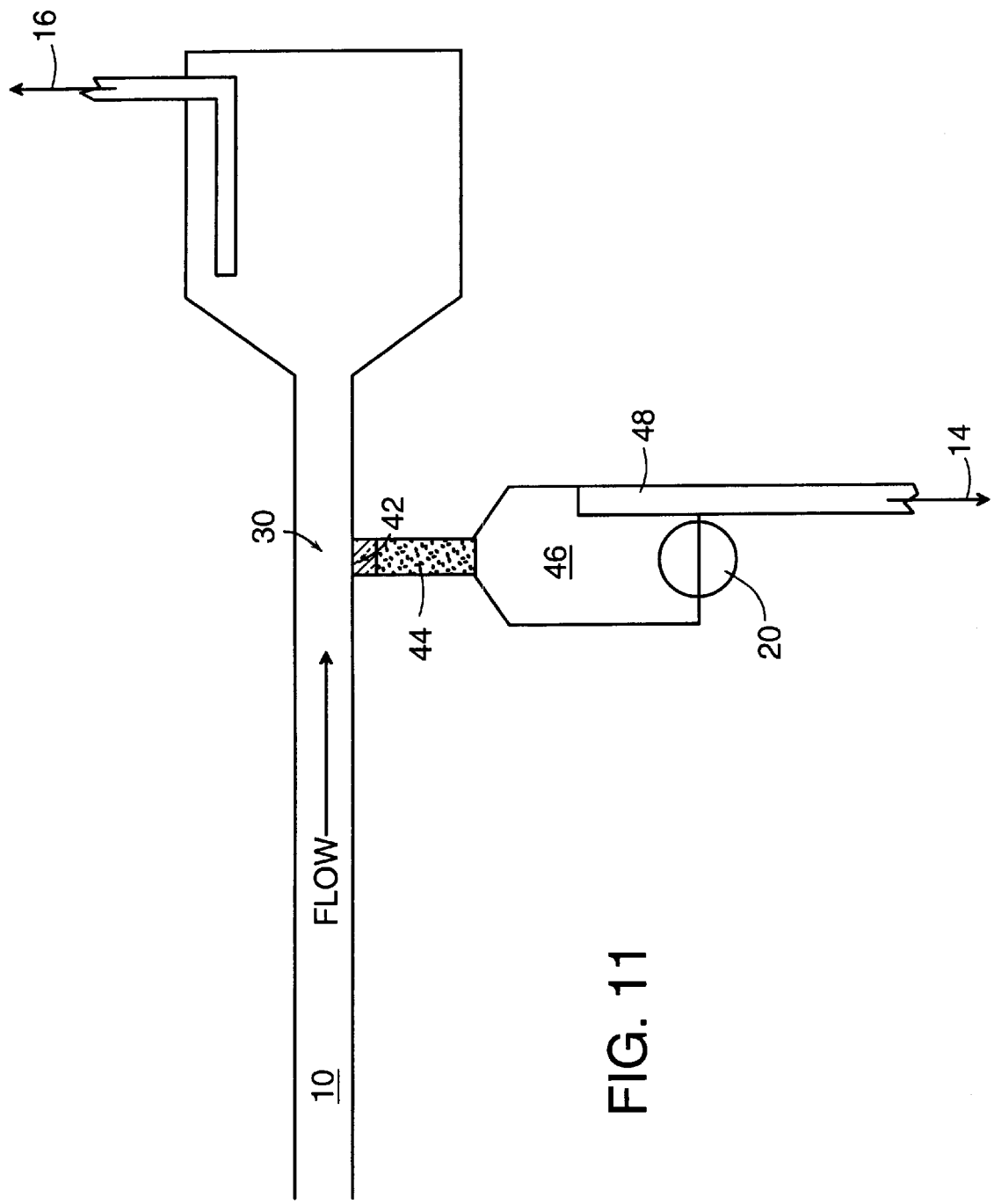
FIG. 11 illustrates an on-chip arrangement for potentiometric detection comprising a side-channel contacting the separation channel, which is separated by a porous membrane.

FIG. 11 illustrates another preferred on-chip arrangement for potentiometric detection comprising a side-channel contacting the separation channel that is separated by a porous permeable membrane or frit material (e.g., porous glass, frit material, conductive or permeable polymer, or the like), which defines the point of detection in the separation channel. The reservoir at the end of the separation channel is provided with a common electrode, which acts as a high voltage ground.

The side channel is filled with an ion-selective lipophilic membrane phase material and ends with a reservoir. The reservoir is provided with a liquid inlet/outlet port and is filled with an internal filling solution, which in this case is an ion-selective lipophilic membrane phase cocktail of appropriate composition (liquid or polymerized). The lipophilic phase is in contact with an aqueous internal filling solution and a micropatterned Ag/AgCl phase. An additional common-electrode which also serves as the high-voltage ground is patterned in the reservoir behind the separation channel to complete the half-cell thus permitting the measurement of the electromotive force of the passing liquid.

Figure 12:
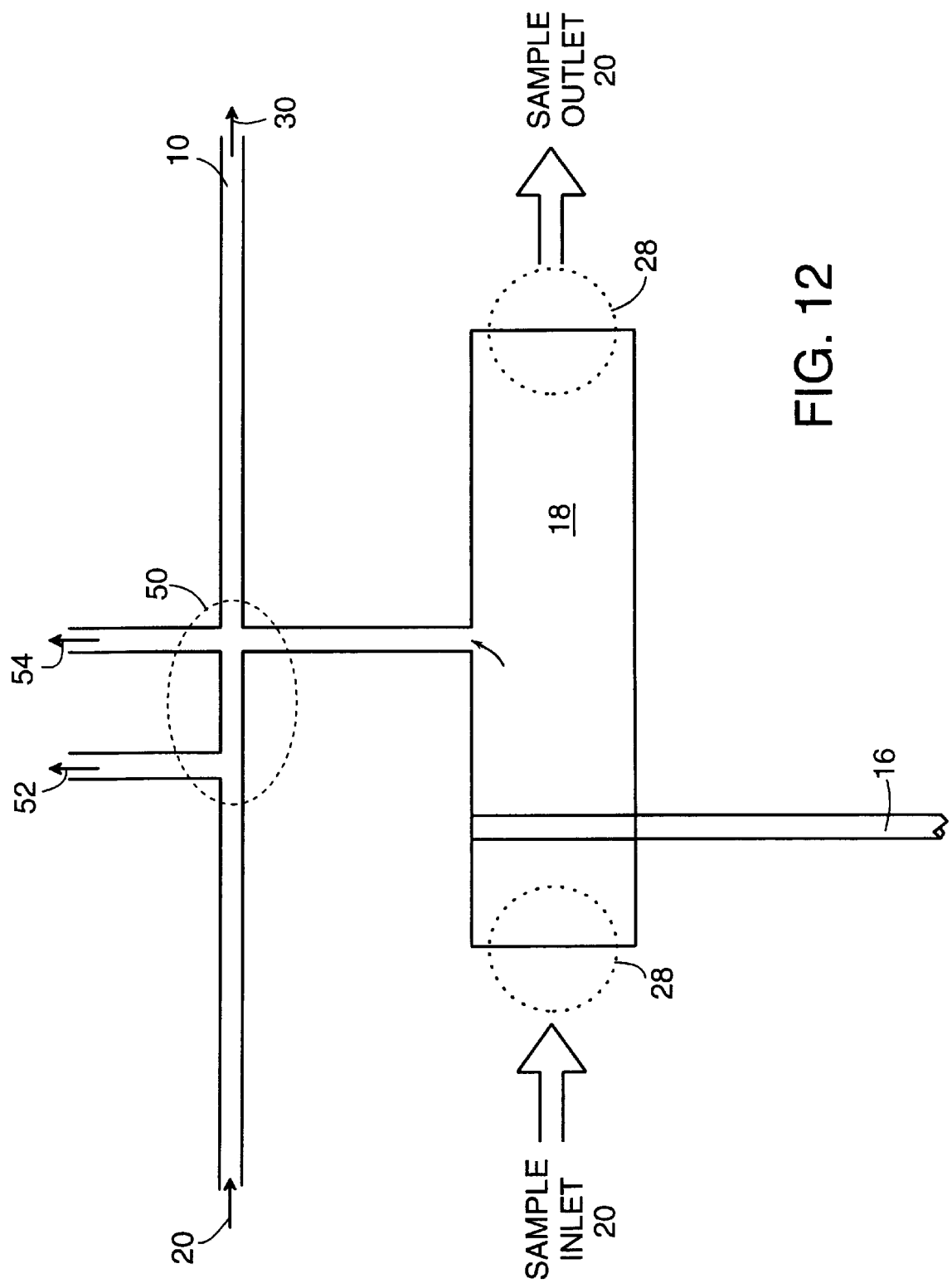
FIG. 12 illustrates a flow injection analysis (FIA)-type on-chip bypass that is connected to the separation channel.

FIG. 12 illustrates a preferred FIA (flow injection analysis)-type single channel, on-chip bypass, which is connected to the separation channel. The bypass channel includes a sample inlet and a waste outlet and the large bypass-channel geometry decreases the flow resistance thereby allowing higher sample throughput. A high voltage electrode is in contact with the bypass channel and by applying a voltage pulse of appropriate polarity, a sample is driven from the FIA-bypass into the injection manifold of the separation channel. The separation channel includes an electrolyte inlet at the left side and the detection area at the right side. Two side channels (sample and waste) are also provided near the injection region.

Figure 13:
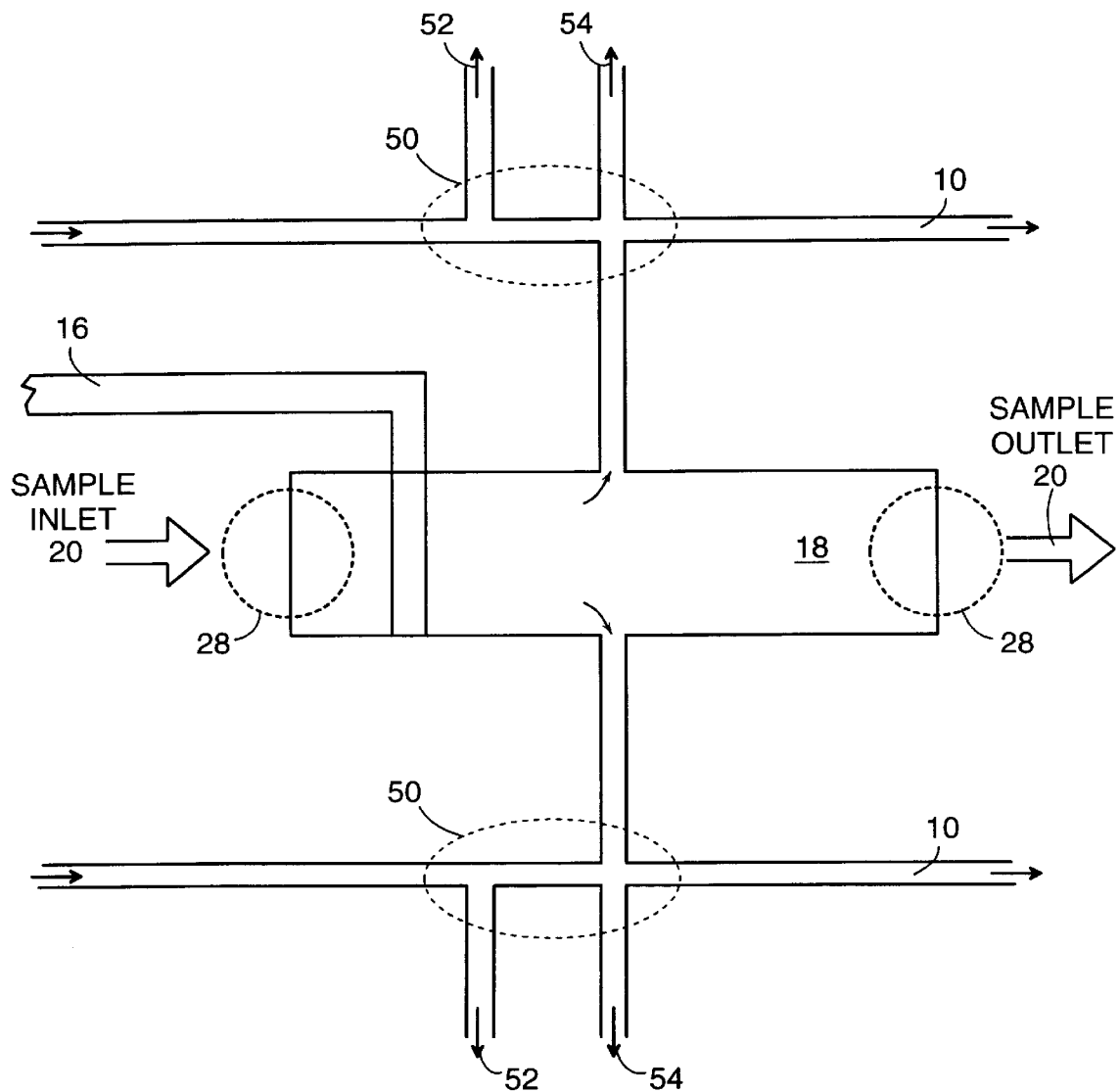
FIG. 13 shows a similar arrangement whereby the FIA-type bypass is connected to two separation manifolds.
Figure 14:
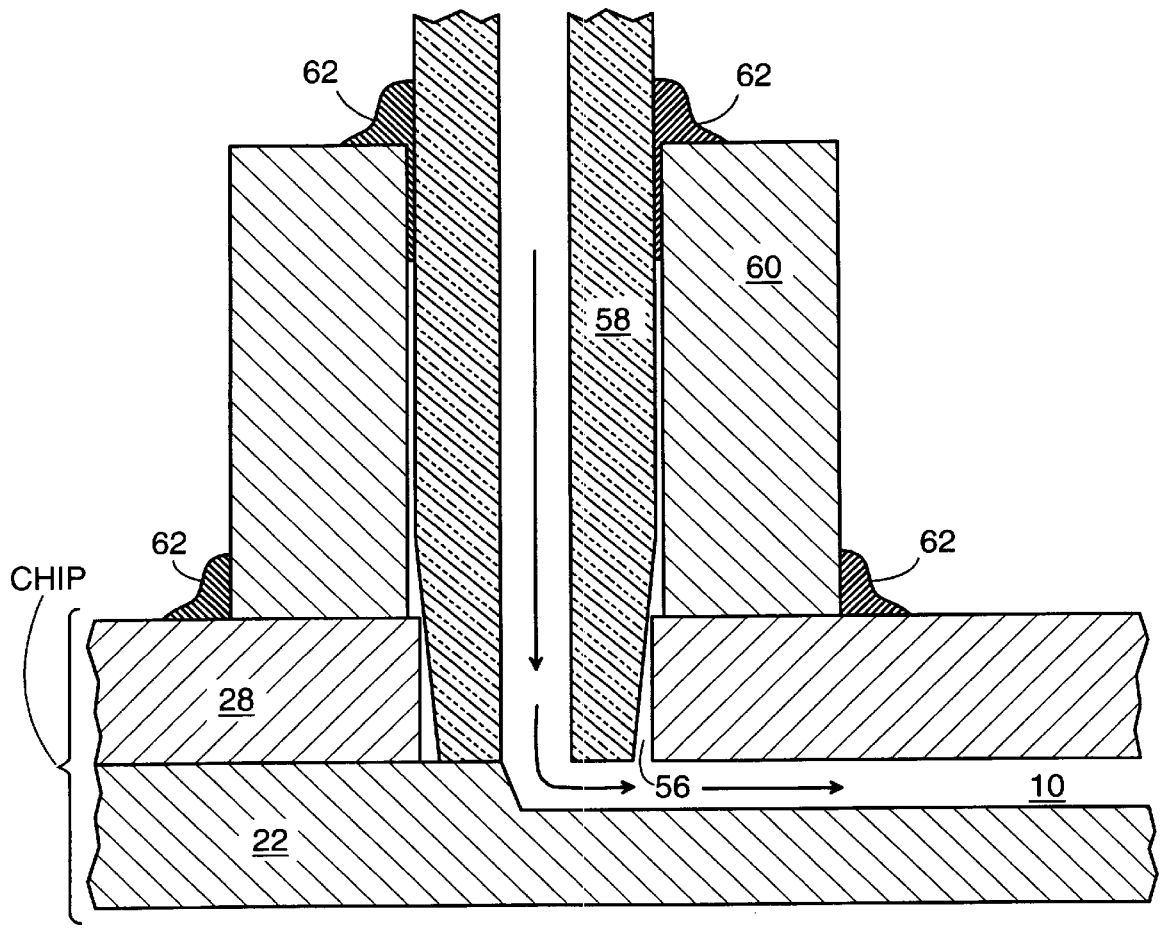
FIG. 14 illustrates a means to connect fused-silica capillary and another material to the appropriate inlet-outlet ports on the chip.

FIG. 13 shows a similar arrangement to that of FIG. 12, but in this case the FIA-type bypass a multiple channel form. As illustrated, the bypass channel is connected to two distinct separation channels; a cation channel and an anion channel. In this case, separate cation and anion electrolytes solutions are employed in their respective separation channels FIG. 14 illustrates a preferred construction method for connecting a fused-silica capillary (of variable internal diameter) or other tubing of similar dimensions and material (e.g., plastic, Teflon, PEEK, and the like) to the appropriate inlet-outlet ports on the chip. The method entails use of a ferrule or other cylindrical object with an adequate-size opening which is precisely centered and immobilized or fixed (e.g., glue, epoxy, UV-curing adhesive, and the like) on the chip. The capillary tubing is pushed through the opening and fixed/immobilized/glued in place. The ferrule permits precise alignment and strain-relief connection for the capillary.

In each illustrated chip embodiment, a manifold of trenches (e.g., from about 10–100 $\mu$m wide, and 20–50 $\mu$m deep) is patterned onto a planar wafer (typically several centimeters in length and width, see FIG. 1) using available micromachining techniques, including for example, photo-lithographical and wet-chemical etching procedures, laser ablation, electroforming-, microcontact printing-, microstamping-, micromolding-, microcasting-, embossing techniques.

Preferably, the chip can be made of glass or plastic and comprises a lower wafer, which holds the trench structure, and an upper wafer, which has holes at appropriate positions for filling the resulting channels with liquid. Both wafers are clamped or bonded together (e.g., thermally) to form a sealed channel manifold.

The injection side of each chip is characterized by a number of channels (typically of similar diameter, see FIG. 1A) which intersect the separation channel at various positions to form a series of microloops for fixed volume sample injection. Each individual channel inlet and outlet on the final structure is in contact with a metal electrode (which may be patterned directly onto the chip) for applying a voltage in the order of 10–10000 Volts, which will propel liquids electrokinetically through the microloops.

The injection manifold may be connected to a larger FIA-bypass flow-through channel (several millimeters in length and 0.3 to 1 millimeters wide) which is patterned onto the bottom wafer and equipped with individual inlet and outlet ports (see, FIGS. 1, 12, 13). The bypass is set for a constant feed-through of sample solution (either by pressurizing its inlet or suction from its outlet port). Applying a voltage between the FIA-bypass and the injection loop manifold will result in electrokinetic injection of fluid having the current sample composition as the fluid in the FIA-bypass. One FIA flow-bypass may be connected to multiple separation manifolds (see, FIG. 13)

The separation channel (typically about 10–100 $\mu$m wide, and about 20–50 $\mu$m deep) connects the injection manifold with the detection electrodes and can be several centimeters long. This channel can be straight (see, FIG. 1) or may be serpentined (not shown) to allow-for a size-compact layout in order to minimize chip dimensions or arrange multiple fluidic microsystems on one single chip. There can be several separation channels, each operated at different polarities and voltages (+/−10 to 10000 V), on one single chip, e.g., one channel dedicated to anion analysis and a parallel channel to cation analysis (experimental conditions set accordingly with the corresponding electrolyte chemistries, flow conditions and appropriate high-voltage polarities).

The detection electrodes (width 10–100 $\mu$m, thickness—depending on the metal deposition process—nm to $\mu$m range) at the end of the separation channel (see FIG. 1B) can be brought onto the wafer by metal vapor deposition or sputtering techniques. Each metal electrode is in physical contact with the fluid in the separation channel.

In the case of contactless high-frequency conductiometric detection, the metal phase is deposited or sputtered into a recess above and below the separation channel (see, FIGS. 8 and 8A). In this case, the electrodes are separated by a thin layer of glass from direct contact with the liquid in the separation channel.

All metal electrodes are conducted toward the edges of the wafer and terminate into accessible contact pads, each several millimeters in length and width. The metal band electrodes can be designed in different preferred ways:

(a) The metal electrodes can be directly deposited on the lower wafer which holds the channel structure and is sealed by thermally bonding the upper glass wafer on the top.

(b) The metal electrodes can be deposited into a prefabricated recess, which potentially might allow for the band electrode layer to be thicker. A safer approach toward a better seal between the wafer components in the detection area (especially to prevent possible leakage around the electrodes), can be achieved by matching the recess depth on the wafer and the deposition thickness of the metal layer.

(c) The detection electrodes can be alternatively patterned onto the upper wafer (see, FIG. 2A). In this case, the two wafers must be precisely aligned before bonding to ensure that the opposed electrodes protrude equally over the width of the separation channel.

(d) The detection electrodes can be patterned as a thin film diametrically opposed on the trapezoidal channel walls (on-column position). This has the advantage that the metal can be deposited as a thin layer to yield a large contact surface.

(e) Instead of one conductive lead per electrode, an additional contact lead can be attached to the onset of the band electrode protruding into the channel (see, FIG. 3) The signal measurement with the double-lead per electrode is superior for unbiased signal transduction.

(f) Two pairs of metal band electrodes can be patterned diametrically opposed on the trapezoidal channel walls (on-column position, see, FIGS. 4 and 4A). The four-electrode arrangement minimizes effects from electrode polarization and contamination, as well as error from cable- and connector resistance. Drive (current) electrodes and sense (voltage) electrodes may differ in size and position arrangement.

(g) One or multiple pairs of metal electrodes may be patterned behind the end of the separation channel into a larger opening thereof, in order to reduce the current density and minimize faradaic interferences on the electrode surface (e.g., gas formation leading to noise, drift) at the point of detection.

(h) Another preferred design comprises one band electrode patterned onto the bottom channel, whereas the second electrode is patterned on the top wafer in a way that the channel-exposed sensing portion of the top electrode is precisely aligned over the sensing portion of the bottom electrode (see, FIGS. 6 and 6A). The corresponding leads are offset in order to avoid direct contact, when the two wafers are bonded together. This design maximizes the sensing area of the electrical and/or electrochemical detector while maintaining on-column geometrical arrangement of the electrodes ('floor-ceiling' design).

(i) The set of electrodes may also be positioned behind the separation channel in a larger reservoir (see, FIG. 7) in order to reduce the current density and related detrimental effects (e.g., gas formation on the electrode leading to noise, drift).

(j) The metal electrodes may be patterned into a prefabricated recess, which is etched into the top and bottom wafer and in exact alignment with the separation channel. A remaining thin layer of glass on the bottom of each recess provides the surface for the metal-deposition and physically isolates the patterned electrodes from the liquid in the channel. The contactless conductivity measurement is carried out by applying a high-frequency AC waveform to the electrodes.

(k) Suppressed on-chip conductiometric detection for electrophoretic ion-analysis is achieved by mixing the effluent post-column (behind the channel) with suppressor liquid of appropriate composition (e.g., microemulsion, see, FIG. 9). The chemical suppression sharply reduces the background conductivity of the electrolyte. The electrophoretic current therefore must be grounded prior to the point of detection.

This can be achieved by microfabricating a porous (conductive) membrane upstream (e.g., porous glass, frit material, conductive or permeable polymer, etc.) to enable the appropriate electrophoretic ion transport to the high-voltage ground which is located in a reservoir off the separation channel. The fluid is then pumped by the momentum of the electroosmotic flow through a first set of detection electrodes and into a mixing 'T', where it reacts with suppressor liquid. The suppressed background electrolyte is pushed hydrodynamically through a second set of detection electrodes. The arrangement allows for significantly lower detection limits as compared to non-suppressed conductivity detection.

(l) On-chip background suppression can be alternatively achieved by appropriate ion-exchange reaction via a porous glass membrane microfabricated upstream before the point of detection (see, FIG. 10). Cations in the electrolyte are replaced with hydronium ions. The weak acid background electrolyte is transformed into a protonated form of low conductivity. The suppressor-joint also serves as an electrophoretic ground junction for the high-voltage, thereby protecting the conductivity cell from the effects of high current-density (signal drift, noise, breakdown of current due to faradaic gas formation on the electrode surface). Overall detection limits are decreased 25–100 fold.

(m) A potentiometric on-chip detection design for electrophoretic ion-analysis consists of a side-channel being in electrical contact with the separation channel (see, FIG. 11). The side channel contains an ion-selective liquid or polymerized membrane phase of specified composition and is separated from the liquid in the separation channel by means of a porous membrane (e.g., porous glass, frit material, conductive or permeable polymer, etc). The organic ion-selective membrane phase is contacted with an aqueous internal filling solution and reference electrode (chloridized silver-phase (Ag/AgCl) which is deposited into the side channel reservoir. The second half-cell and potentiometric reference point is formed by a 'common-electrode', which may be patterned into the reservoir-outlet behind the separation channel. This band electrode is preferentially made of platinum (Pt) and may serve as the electrohoretic high-voltage ground.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A capillary electrophoretic separation system formed on a planar chip, said planar chip comprising at least two wafers, one or more of which is provided with one or more separation channels and one or more integrated electrodes in communication with said separation channels, said electrodes arranged in an array design selected from the group consisting of: (a) on-column, (b) end-column, (c) off-column and (d) contactless high-frequency.

2. The electrophoretic separation system of claim 1, wherein the electrode array is an on-column design, wherein one or more electrodes are patterned directly into one or more separation channels.

3. The electrophoretic separation system of claim 2, wherein a separation channel and electrode pattern is located in the uppermost wafer of the planar chip.

4. The electrophoretic separation system of claim 2, wherein a separation channel and electrode pattern is located in the bottom wafer of the planar chip.

5. The electrophoretic separation system of claim 2, wherein a separation channel and electrode pattern is provided in both the uppermost and the bottom wafers of the planar chip.

6. The electrophoretic separation system of claims 2, 3, 4 or 5, wherein the electrode pattern comprises multiple electrodes per channel.

7. The electrophoretic separation system of claim 1, wherein the electrode array is an end-column design, wherein one or more electrodes patterned at a short distance behind the separation channel in an electrically grounded reservoir.

8. The electrophoretic separation system of claim 7, wherein a separation channel and electrode pattern is located in the uppermost wafer of the planar chip.

9. The electrophoretic separation system of claim 7, wherein a separation channel and electrode pattern is located in the bottom wafer of the planar chip.

10. The electrophoretic separation system of claim 7, wherein a separation channel and electrode pattern is provided in both the uppermost and the bottom wafers of the planar chip.

11. The electrophoretic separation system of claims 7, 8, 9 or 10, wherein the electrode pattern comprises multiple electrodes per channel.

12. The electrophoretic separation system of claim 1, wherein the electrode array is an off-column electrode design, wherein the detection electrodes are patterned downstream of a conductive joint, which shunts off the electrophoretic current prior to the point of detection.

13. The electrophoretic separation system of claim 12, wherein a separation channel and electrode pattern is located in the uppermost wafer of the planar chip.

14. The electrophoretic separation system of claim 12, wherein a separation channel and electrode pattern is located in the bottom wafer of the planar chip.

15. The electrophoretic separation system of claim 12, wherein a separation channel and electrode pattern is provided in both the uppermost and the bottom wafers of the planar chip.

16. The electrophoretic separation system of claims 12, 13, 14 or 15, wherein the electrode pattern comprises multiple electrodes per channel.

17. The electrophoretic separation system of claim 1, wherein the electrode array is a contactless electrode design, wherein the electrodes are patterned into a recess on top and on the bottom of the separation wafer with a thin layer of glass separating the active metal from the fluid in the separation channel.

* * * * *